(12) United States Patent
Kato et al.

(10) Patent No.: US 10,197,511 B2
(45) Date of Patent: Feb. 5, 2019

(54) X-RAY CT APPARATUS AND X-RAY DETECTOR WITH VARIABLE LAYER

(71) Applicant: TOSHIBA MEDICAL SYSTEMS CORPORATION, Otawara-Shi (JP)

(72) Inventors: Tooru Kato, Nasushiobara (JP); Hiroaki Nakai, Nasushiobara (JP); Mikihito Hayashi, Otawara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 484 days.

(21) Appl. No.: 14/831,086

(22) Filed: Aug. 20, 2015

(65) Prior Publication Data
US 2016/0054454 A1  Feb. 25, 2016

(30) Foreign Application Priority Data

Aug. 20, 2014 (JP) .................... 2014-167945
Aug. 18, 2015 (JP) .................... 2015-161065

(51) Int. Cl.
| | |
|---|---|
| *G01T 1/20* | (2006.01) |
| *G01N 23/046* | (2018.01) |
| *G01T 1/17* | (2006.01) |
| *G01T 1/29* | (2006.01) |

(52) U.S. Cl.
CPC .......... *G01N 23/046* (2013.01); *G01T 1/17* (2013.01); *G01T 1/2002* (2013.01); *G01T 1/2985* (2013.01); *G01N 2223/505* (2013.01)

(58) Field of Classification Search
CPC ........ G01T 1/2002; G01T 1/17; G01N 23/046
USPC ........................................... 385/141
See application file for complete search history.

(56) References Cited

U.S. PATENT DOCUMENTS

| | | | | |
|---|---|---|---|---|
| 5,616,924 A | * | 4/1997 | Petrillo | G01T 1/1642 250/368 |
| 7,332,723 B2 | * | 2/2008 | Histrov | G01T 1/2018 250/368 |
| 7,375,341 B1 | * | 5/2008 | Nagarkar | G01T 1/2002 250/370.11 |

(Continued)

FOREIGN PATENT DOCUMENTS

| | | |
|---|---|---|
| JP | 2002-306464 | 10/2002 |
| JP | 2007-526475 | 9/2007 |

(Continued)

*Primary Examiner* — Yara B Green
(74) *Attorney, Agent, or Firm* — Oblon, McClelland, Maier & Neustadt, L.L.P.

(57) ABSTRACT

An X-ray computer tomography (CT) apparatus according to an embodiment includes an X-ray source, an X-ray detector, and generating circuitry. The X-ray source radiates X-rays. The X-ray detector includes a scintillator including a first region close to the X-ray source and a second region distant from the X-ray source, an optical sensor that detects scintillator light obtained by converting the X-rays radiated from the X-ray source with the scintillator, and a variable layer that is provided in the scintillator and switchable between a first state in which the variable layer transmits the scintillator light between the first region and the second region and a second state in which the variable layer does not transmit the scintillator light between the first region and the second region. The generating circuitry generates a CT image based on a signal output from the X-ray detector.

21 Claims, 23 Drawing Sheets

(56) References Cited

U.S. PATENT DOCUMENTS

| | | | |
|---|---|---|---|
| 7,738,625 B2 | 6/2010 | Nishide et al. | |
| 8,243,874 B2 | 8/2012 | Carmi | |
| 8,384,034 B2 | 2/2013 | Nakamura | |
| 2003/0195416 A1* | 10/2003 | Toth | A61B 6/032 600/427 |
| 2008/0290280 A1 | 11/2008 | Ruetten et al. | |
| 2008/0293666 A1* | 11/2008 | Aldrich | C07D 209/08 514/47 |
| 2009/0134334 A1* | 5/2009 | Nelson | G01T 1/2002 250/361 R |
| 2012/0220833 A1* | 8/2012 | Ehrenreich | A61B 1/32 600/219 |
| 2013/0327947 A1* | 12/2013 | Ronda | G01T 1/1644 250/362 |
| 2014/0151562 A1* | 6/2014 | Wang | G01T 1/2002 250/362 |

FOREIGN PATENT DOCUMENTS

| | | |
|---|---|---|
| JP | 2011-112623 | 6/2011 |
| JP | 2011-203237 | 10/2011 |
| JP | 5582514 | 9/2014 |
| JP | 5647293 | 12/2014 |
| WO | WO 2009/037781 A1 | 3/2009 |

* cited by examiner

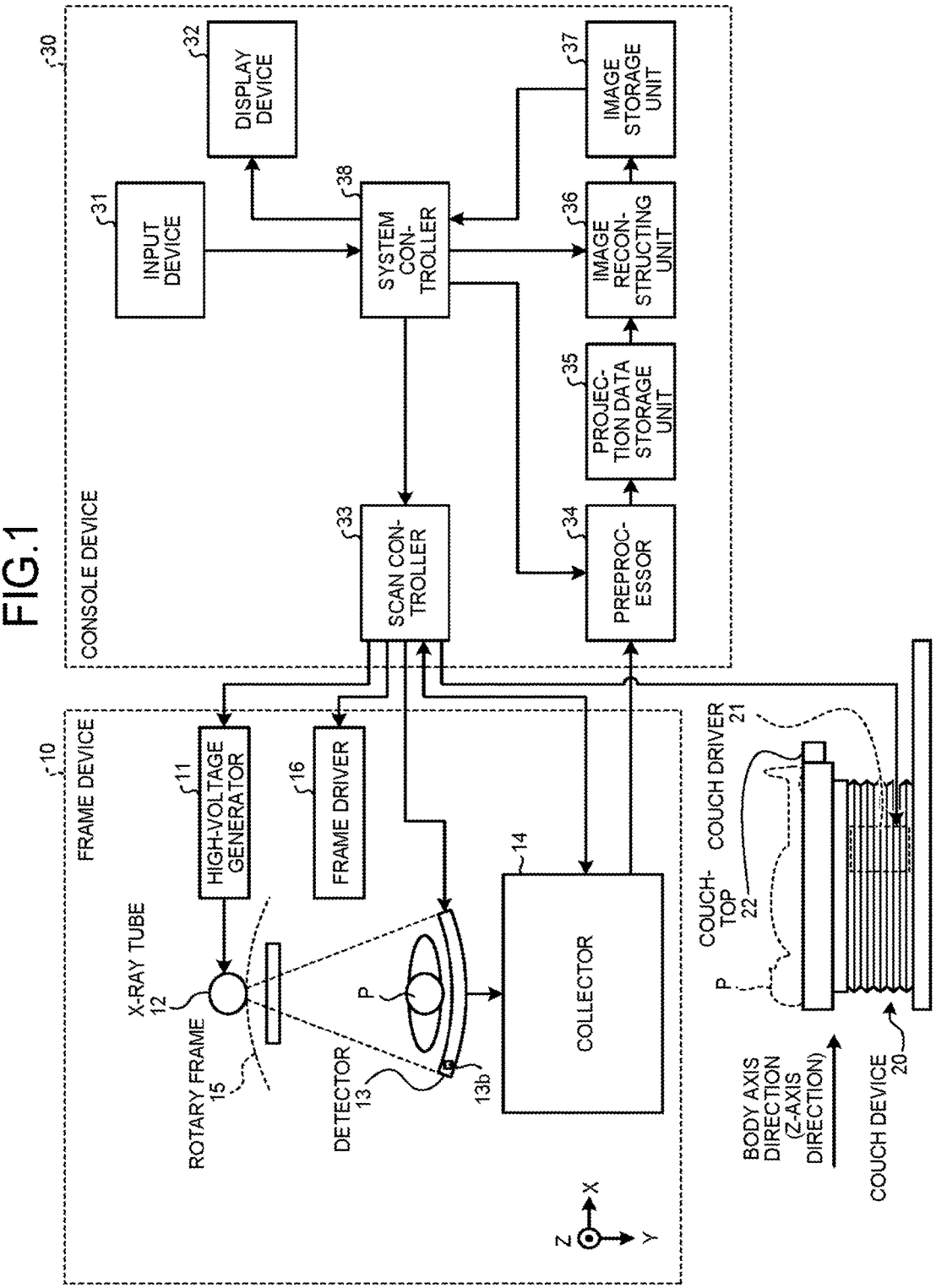

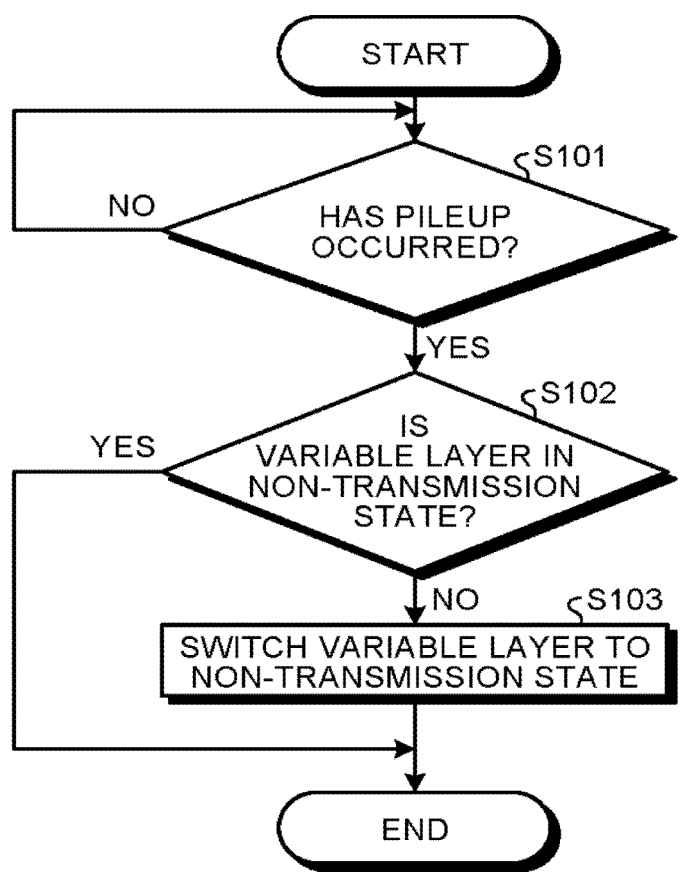

X-RAY CT APPARATUS AND X-RAY DETECTOR WITH VARIABLE LAYER

CROSS-REFERENCE TO RELATED APPLICATIONS

This application is based upon and claims the benefit of priority from Japanese Patent Application No. 2014-167945, filed on Aug. 20, 2011 and No. 2015-161065, filed on Aug. 18, 2015; the entire contents of which are incorporated herein by reference.

FIELD

Embodiments described herein relate generally to an X-ray computer tomography (CT) apparatus and an X-ray detector.

BACKGROUND

In recent years, X-ray CT apparatuses using a photon counting detector have been developed. Photon counting detectors individually count light derived from X-rays that have passed through the subject, unlike integral detectors used in X-ray CT apparatuses in related art. For this reason, X-ray CT apparatuses using a photon counting detector are capable of reconstructing X-ray CT images with a high signal per noise (SN) ratio. In addition, photon counting enables identification of substance using difference in K absorption edge, because photon counting enables imaging from X-ray output of a single type divided into a plurality of energy components.

BRIEF DESCRIPTION OF THE DRAWINGS

FIG. 1 is a diagram illustrating a configuration example of an X-ray computer tomography (CT) apparatus according to a first embodiment;

FIG. 6 is a flowchart illustrating a procedure of processing performed by a switching controller according to the first embodiment;

DETAILED DESCRIPTION

Figure 2A:
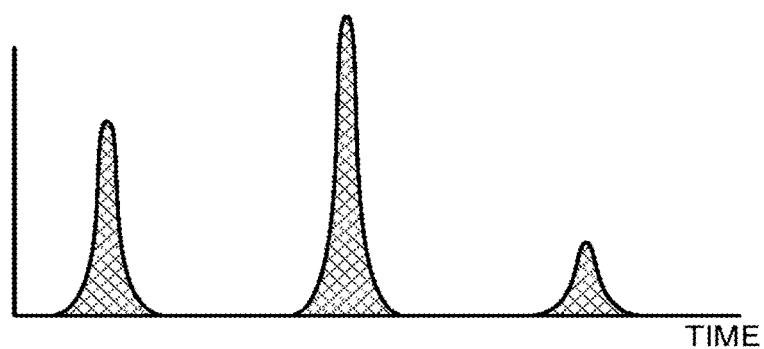
FIG. 2A is a diagram for explaining pileup in an optical sensor according to related art.

An X-ray computer tomography (CT) apparatus and an X-ray detector according to embodiments will be described hereinafter with reference to drawings.

An X-ray CT apparatus explained in the following embodiments is an apparatus capable of performing photon counting CT. Specifically, the X-ray CT apparatus explained in the following embodiments is an apparatus that counts X-rays that have passed through the subject using a photon counting detector, not a conventional integral (current mode measuring) detector, to reconstruct X-ray CT image data with a high SN ratio.

An X-ray computer tomography (CT) apparatus according to an embodiment includes an X-ray source, an X-ray detector, and generating circuitry. The X-ray source radiates X-rays. The X-ray detector includes a scintillator including a first region close to the X-ray source and a second region distant from the X-ray source, an optical sensor that detects scintillator light obtained by converting the X-rays radiated from the X-ray source with the scintillator, and a variable layer that is provided in the scintillator and switchable between a first state in which the variable layer transmits the scintillator light between the first region and the second region and a second state in which the variable layer does not transmit the scintillator light between the first region and the second region. The generating circuitry generates a CT image based on a signal output from the X-ray detector.

First Embodiment

FIG. 1 is a diagram illustrating a configuration example of an X-ray CT apparatus according to a first embodiment. As illustrated in FIG. 1, the X-ray CT apparatus according to the first embodiment includes a frame device 10, a couch device 20, and a console device 30.

The frame device 10 is a device that applies X-rays to the subject P to collect data related to the X-rays that have passed through the subject P. The frame device 10 includes a high-voltage generator 11, an X-ray tube 12, a detector 13, a collector 14, a rotary frame 15, and a frame driver 16.

The rotary frame 15 is a circular frame that supports the X-ray tube 12 and the detector 13 to the opposed to each other with the subject P interposed therebetween, and is rotated at high speed along a circular track with the subject P serving as the center by the frame driver 16 described later.

The X-ray tube 12 is a vacuum tube that applies an X-ray beam to the subject P with high voltage supplied from the high-voltage generator 11 described later. The X-ray tube 12 applies an X-ray beam to the subject P with rotation of the rotary frame 15. The X-ray tube 12 serves as an X-ray source that radiates X-rays.

The high-voltage generator 11 is a device that supplies high voltage to the X-ray tube 12. The X-ray tube 12 generates X-rays using high voltage supplied from the high-voltage generator 11. Specifically, the high-voltage generator 11 regulates the X-ray dose applied to the subject P by regulating the tube voltage or the tube current supplied to the X-ray tube 12.

The frame driver 16 rotates and drives the rotary frame 15, to revolve the X-ray tube 12 and the detector 13 on the circular track with the subject P serving as the center.

The detector 13 includes a plurality of detection elements to count light derived from the X-rays that have passed through the subject P. As an example, the detection elements included in the detector 13 according to the first embodiment are detectors of an indirect conversion type, each of which is formed of a scintillator and an optical sensor. The details of the detector 13 will be described later with reference to FIG. 4A and FIG. 4B. The detector 13 is provided with a switching controller 13b described later.

With reference to FIG. 1 again, the collector 14 collects a counting result serving as a result of counting processing using output signals of the detector 13. The collector 14 counts the number of photons (X-ray photons) derived from the X-rays that were applied from the X-ray tube 12 and passed through the subject P, to collect a result of discriminating energy of the counted photons as the counting result. The collector 14 transmits the counting result to the console device 30.

Specifically, the collector 14 collects incident positions (detection positions) of the X-ray photons counted by discriminating each of the pulses output by the detection elements and the energy values of the X-ray photons as the counting result, for each phase (tube phase) of the X-ray tube 12. For example, the collector 14 collects the position of the detection element that outputs the pulse used for counting, as the incident, position. The collector 14 calculates, for example, the energy value from the peak value of the pulse and a response function peculiar to the system. As another example, the collector 14 calculates the energy value by integrating the intensity of the pulse. The collector 14 distributes the calculated energy values (E) into a plurality of energy discriminating regions.

The collector 14 according to the present embodiment distributes the calculated energy values into a plurality of energy discriminating regions using a comparator, for example. The energy discriminating regions are energy division sets that are set using thresholds to distribute the energy values into energy ranges of certain particle sizes by the collector 14.

For example, the counting result collected by the collector 14 is information that "the counting value photons in the energy discriminating region 'E1<E≤E2' is 'N1', and the counting value of photons in the energy discriminating region 'E2<E≤E3' is 'P2', in the detection element at the incident position 'P11' at the tube phase 'α1'". As another example, the counting result collected by the collector 14 is information that "the counting value of photons per unit time in the energy discriminating region 'E1<E≤E2' is 'n1', and the counting value of photons per unit time in the energy discriminating region 'E2<E≤E3' is 'n2', in the detection element at the incident position 'P11' at the tube phase 'α1'".

The couch device 20 is a device on which the subject P is placed. The couch device 20 includes a couchtop 22 and a couch driver 21. The couchtop 22 is a plate on which the subject P is placed. The couch driver 21 moves the couchtop 22 in the Z-axis direction, to move the subject P into the rotary frame 15.

For example, the frame device 10 executes helical scan to helically scan the subject P by rotating the rotary frame 15 while the couchtop 22 is moved. As another example, the frame device 10 executes conventional scan to scan the subject P with a circular track by rotating the rotary frame 15 with the position of the subject P fixed after the couchtop 22 is moved.

The console device 30 is a device that receives operations of the X-ray CT apparatus that are performed by the operator, and reconstructs X-ray CT image data using counting information collected by the frame device 10. As illustrated in FIG. 1, the console device 30 includes an input device 31, a display device 32, a scan controller 33, a preprocessor 34, a projection data storage unit 35, an image reconstructing unit 36, an image storage unit 37, and a system controller 38.

The input device 31 includes a mouse, a keyboard, and the like used by the operator of the X-ray CT apparatus for inputting various instructions and various settings. The input device 31 transmits information of instructions and settings received from the operator to the system controller 38. For example, the input device 31 receives reconstructing conditions used for reconstructing X-ray CT image data, and image processing condition for X-ray CT image data from the operator.

The display device 32 is a monitor that the operator refers to. The display device 32 displays X-ray CT image data for the operator, and displays graphical user interface (GUI) to receive various instructions and various settings from the operator via the input device 31, under the control of the system controller 38.

The scan controller 33 controls operations of the high-voltage generator 11, the frame driver 16, the collector 14, and the couch driver 21 under the control of the system controller 38 described later, to control counting information collection processing in the frame device 10.

The preprocessor 34 subjects the counting result transmitted from the collector 14 to correction processing such as logarithmic transformation, offset correction, sensitivity correction, and beam hardening correction, to generate projection data for each energy discriminating region.

The projection data storage unit 35 stores therein projection data generated by the preprocessor 34. Specifically, the projection data storage unit 35 stores therein projection data for reconstructing X-ray CT image data.

The image reconstructing unit 36 generates a CT image based on a signal output by the detector 13. The image reconstructing unit 36 performs, for example, back projection processing on the projection data stored in the projection data storage unit 35, to reconstruct X-ray CT image data. An example of the back projection processing is back projection processing using filtered back projection (FBP). The image reconstructing unit 36 may perform reconstruction by, for example, successive approximation. The image reconstructing unit 36 also performs various image processing on X-ray CT image data to generate image data. The image reconstructing unit 36 stores the reconstructed X-ray CT image data and image data generated by various image processing in the image storage unit 37.

The projection data generated from the counting result obtained by photon counting CT includes information of the energy of the X-rays attenuated by passing through the subject P. For this reason, for example, the image reconstructing unit can reconstruct X-ray CT image data of a specific energy component. The image reconstructing unit 36 can also reconstruct X-ray CT image data of respective energy components.

For example, the image reconstructing unit 36 can assign color tones corresponding to the energy components to the pixels of the X-ray CT image data of the respective energy components, to generate image data obtained by superimposing a plurality of pieces of X-ray CT image data with different colors according to the energy components. The image reconstructing unit 36 can also generate image data that enables identification of a substance using the K absorption edge peculiar to the substance. Examples of other image data generated by the image reconstructing unit 36 are single-color X-ray image data, density image data, and effective atomic number image data.

The system controller 38 controls operations of the frame device 10, the couch device 20, and the console device 30, to control the whole X-ray CT apparatus. Specifically, the system controller 38 controls the scan controller 33 to control CT scans performed in the frame device 10. The system controller 38 also controls the preprocessor 34 and the image reconstructing unit 36, to control image reconstruction and image generation in the console device 30. The system controller 38 also performs control to cause various image data stored in the image storage unit 37 to be displayed on the display device 32.

Under the whole configuration of the X-ray CT apparatus according to the first embodiment described above, the X-ray CT apparatus according to the first embodiment reconstructs X-ray CT image data using a photon counting detector.

In photon counting CT, the number of photons is counted to measure the quantity of X-rays. The intensity of the X-rays increases as the number of photons per unit time increases. Although individual photons have different energies, photon counting CT enables acquisition of information of the energy component of the X-rays by measuring the energies of the photons. Specifically, photon counting CT enables imaging in which the data collected by applying X-rays with a single type of tube voltage is divided into a plurality of energy components. For example, photon counting CT enables acquisition of image data that enables identification of substance using difference in K absorption edge.

However, "pileup" occurs in photon counting CT, when the incident radiation dose is large. In pileup, data acquired by counting individual photons accumulate. Because individual photons cannot be separated from each other when pileup occurs, "counting loss" occurs in which the counting characteristic is not linear.

Figure 2B:
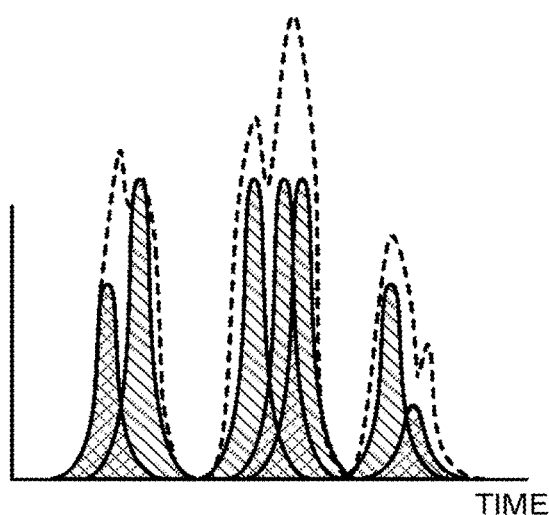
FIG. 2B is a diagram for explaining pileup in an optical sensor according to related art.
Figure 2C:
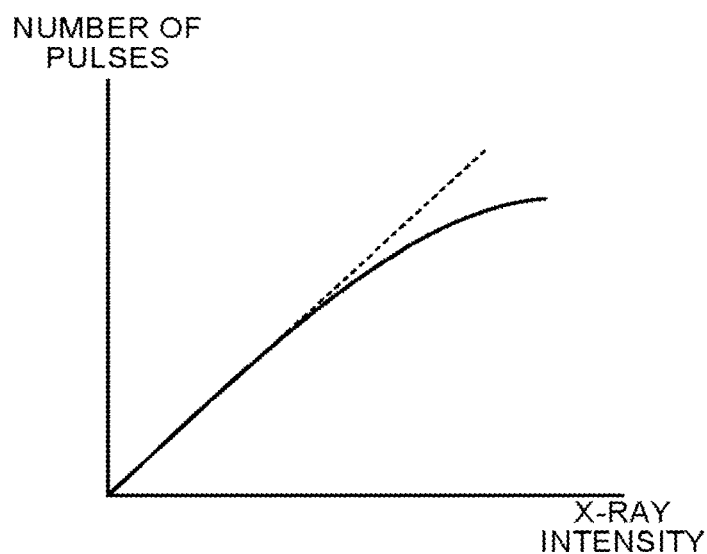
FIG. 2C is a diagram for explaining pileup in an optical sensor according to related art.

FIG. 2A, FIG. 2B, and FIG. 2C are diagrams for explaining pileup in an optical sensor according to related art. When scintillator light is made incident on an optical sensor used in a photon counting detector, the optical sensor outputs an electrical signal of one pulse. When the incident X-rays are weak, because the incident intervals of the scintillator are sparse as illustrated in FIG. 2A, each of pulses that are output from the sensor can be discriminated from each other.

However, when the incident intervals of the scintillates are shortened by increase in the incident X-rays, pulses that are output from the optical sensor pileup as illustrated in FIG. 2B, and the individual pulses cannot be discriminated from each other. Specifically, a plurality of pulses that have piled up are discriminated as one pulse in appearance (see waveforms of dot lines illustrated in FIG. 2B). As a result, counting loss (pileup) occurs, and linearity is lost between the number of scintillator light actually made incident on the optical sensor and the counting value (number of pulses) of pulses that are output by the sensor. Specifically, the number of pulses is counted less than the number of scintillator light as the X-ray intensity increases, as illustrated in FIG. 2C.

Figure 3:
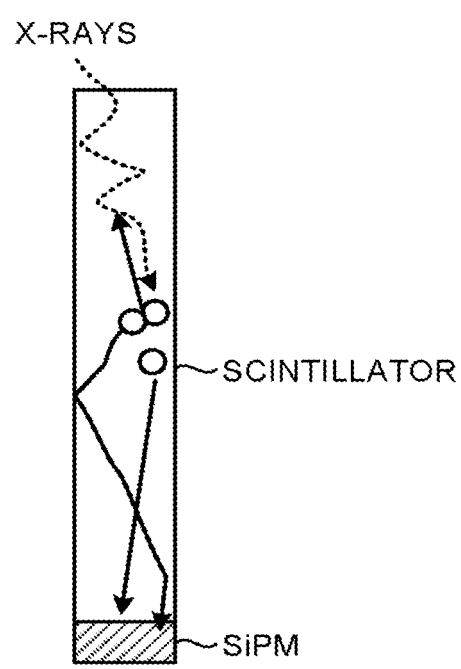
FIG. 3 is a diagram for explaining pileup in a scintillator according to related art.

In addition, when a scintillator is used in the photon-counting sensor, pileup occurs in the scintillates in which X-rays cannot be separated one by one in the scintillator, when the incident X-ray dose increases. Such a case also has the problem that the counting characteristic is not linear. FIG. 3 is a diagram for explaining pileup in a scintillator according to related art. As illustrated in FIG. 3, a silicon photomultiplier (SiPM) serving as an optical sensor is disposed at an end portion on the side opposite to the X-ray incident side in the scintillator according to related art. The scintillator requires a predetermined time for converting X-rays into scintillator light. For this reason, the scintillator according to related art may not be able to convert a newly incident X-ray into scintillator light, when the incident X-ray dose increases and a new X-ray is made incident within the predetermined time required for converting X-rays into scintillator light. In such a case, the detector 13 cannot count the incident X-rays.

Figure 4A:
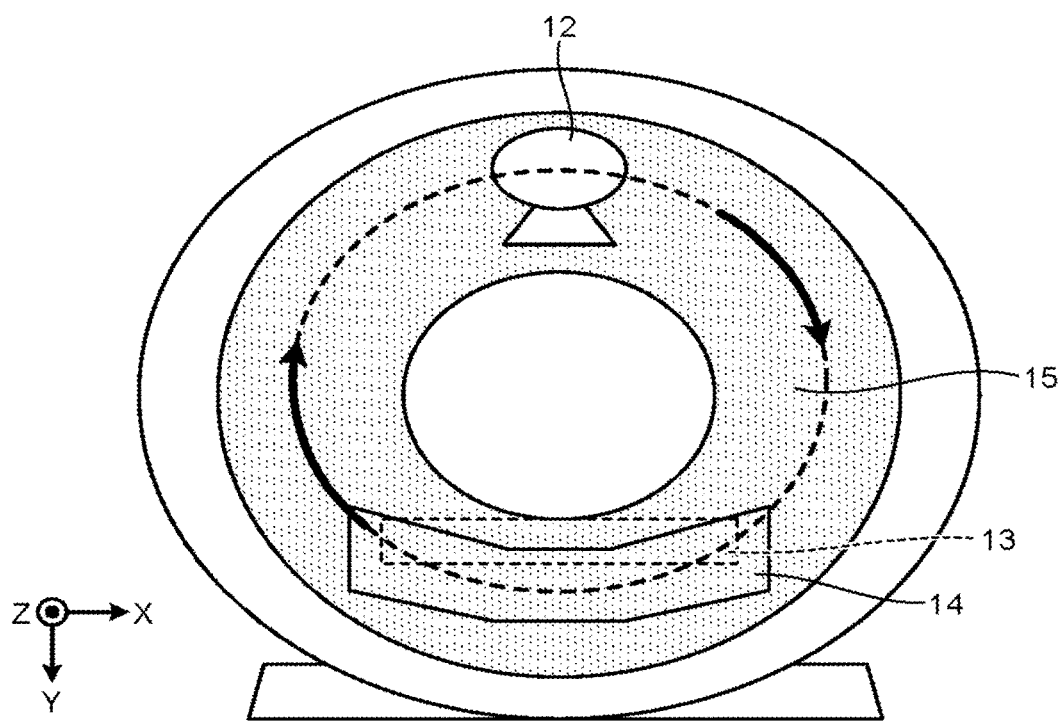
FIG. 4A is a diagram for explaining an example of a detector according to the first embodiment.
Figure 4B:
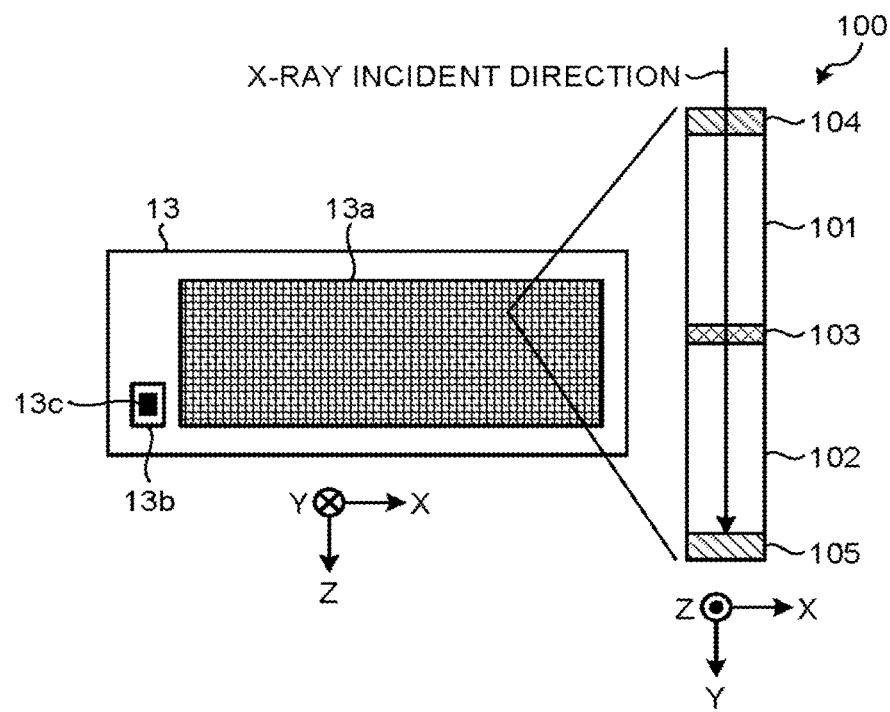
FIG. 4B is a diagram for explaining an example of the detector according to the first embodiment.

To reduce occurrence of counting loss, the detector 13 is configured as follows in the X-ray CT apparatus according to the first embodiment. FIG. 4A and FIG. 4B are diagrams for explaining an example of the detector 13 according to the first embodiment.

FIG. 4A illustrates the case where the frame device 10 is viewed from the front. As illustrated in FIG. 4A, the rotary frame 15 supports the X-ray tube 12 and the detector 13. FIG. 4B illustrates an enlarged view of the detector 13 illustrated in FIG. 4A. FIG. 4B illustrates the case where the detector 13 is viewed from the Y-axis side. As illustrated in FIG. 4B, the detector 13 includes a detection element group 13a and a switching controller 13b.

In the detection element group 13a, detection elements are arranged on the surface in a two-dimensional manner, as illustrated in FIG. 4B. For example, a plurality of detection element lines arranged in a channel direction (the X-axis direction in FIG. 4B) are arranged in a plurality of lines along the body axis direction (the Z-axis direction in FIG. 4B) of the subject P.

The following is explanation of each of the detection elements arranged in the detection element group 13a. Each of the detection elements includes a scintillator having a first region that is close to the X-ray source and a second region that is distant from the X-ray source, and optical sensors that detect scintillator light obtained by converting X-rays radiated from the X-ray source with the scintillator. Each of the detection elements also includes a variable layer that is provided in the scintillator and switchable between a first state in which the variable layer transmits scintillator light between the first region and the second region and a second state in which the variable layer does not transmit scintillator light between the first region and the second region. More specifically, as illustrated in FIG. 4B, each detection element 100 includes scintillators 101 and 102, optical sensors 104 and 105, and a variable layer 103.

The scintillator 101 corresponds to the first region that is close to the X-ray source, and the scintillator 102 corresponds to the second region that is distant from the X-ray source. The scintillators 101 and 102 convert the incident X-rays radiated from the X-ray source into scintillator light. The arrival positions of the incident X-rays in the scintillators 101 and 102 are stochastically determined in accordance with the intensity of the energy of the incident X-rays. For example, incident X-rays having small energy reaches the scintillator 101 side with high probability, and incident X-rays having large energy reaches the scintillator 102 side with high probability.

The optical sensors 104 and 105 are SiPMs, and detect scintillator light converted by the scintillators 101 and 102. The optical sensors 104 and 105 are arranged at both ends in the X-ray incident direction of the scintillators 101 and 102. More specifically, as illustrated in FIG. 4B, the optical sensor 104 is disposed at the end portion on the X-ray incident side of the scintillator 101, and the optical sensor 105 is disposed at the end portion on the side of the scintillator 102 opposed to the X-ray incident side thereof.

The variable layer 103 is provided in the scintillators 101 and 102, and switchable between the first state in which the variable layer 103 transmits scintillator light and the second state in which the variable layer 103 does not transmit scintillator light. In other words, the variable layer 103 is switchable between the first state in which the variable layer 103 transmits scintillator light between the first region and the second region and the second state in which the variable layer 103 does not transmit scintillator light between the first region and the second region. The incident X-rays are transmitted through the variable layer 103, regardless of whether the variable layer 103 is in the first state or in the second state. The variable layer 103 is disposed between the optical sensor 104 and the optical sensor 105 that are disposed at both ends. In the example illustrated in FIG. 4B, the variable layer 103 is disposed in substantially the center of the detection element 100. The variable layer 103 is, for example, a liquid crystal film, a light polarization film, or a micro electro mechanical systems (MEMS) shutter. The variable layer 103 is capable of instantaneously switching, electrically or mechanically, between the first state in which the variable layer 103 transmits scintillator light and the second state in which the variable layer 103 does not transmit scintillator light. The first state and the second state of the variable layer 103 can be controlled as desired for each of the detection elements 100 arranged in the detection element group 13a. In the following explanation, suppose that the variable layer 103 is in the first state in which the variable layer 103 transmits scintillator light at the start of imaging performed by the X-ray CT apparatus, for the sake of convenience of explanation.

The switching controller 13b controls switching of the variable layer 103 between the first state and the second state. As illustrated in FIG. 4B, the switching controller 13b includes a sensor 13c that measures the intensity of the incident X-rays. For example, the switching controller 13b controls switching of the variable layer 103 between the first state and the second state, depending on the intensity of the incident X-rays measured by the sensor 13c. More specifically, the switching controller 13b switches the variable layer 103 from the first state to the second state, when the intensity of the incident X-rays measured by the sensor 13c is higher than a predetermined threshold. The following explanation illustrates the case where pileup occurs when the intensity of the incident X-rays is higher than the predetermined threshold.

Figure 5A:
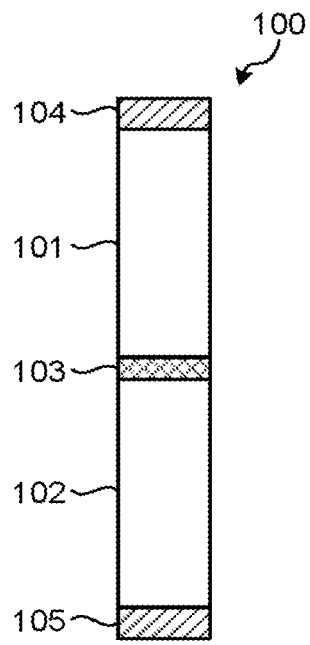
FIG. 5A is a diagram for illustrating a processing operation performed by a detection element according to the first embodiment.
Figure 5B:
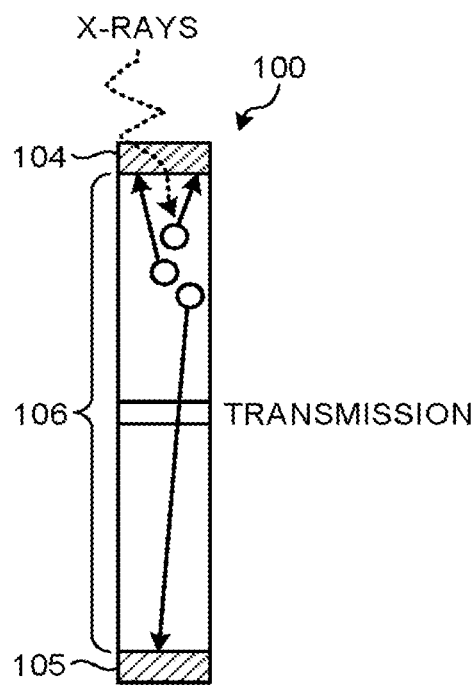
FIG. 5B is a diagram for illustrating a processing operation performed by the detection element according to the first embodiment.
Figure 5C:
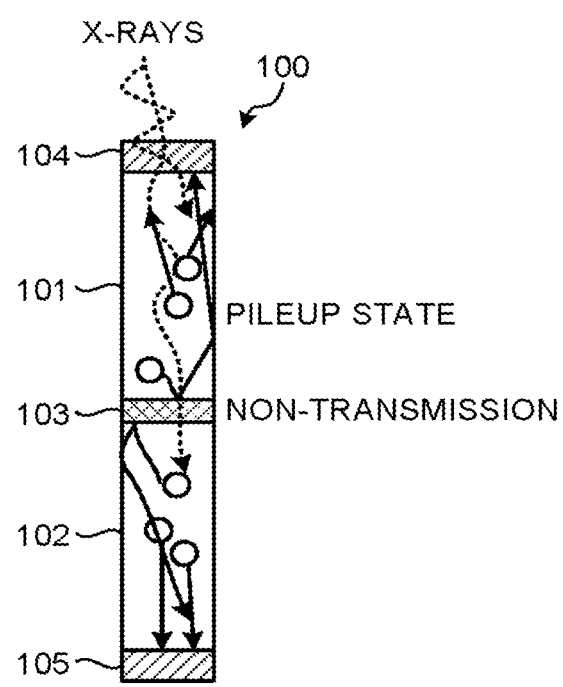
FIG. 5C is a diagram for illustrating a processing operation performed by the detection element according to the first embodiment.

The following is explanation of a processing operation performed by each detection element 100 according to the first embodiment, with reference to FIG. 5A to FIG. 5C. FIG. 5A to FIG. 5C are diagrams for explaining a processing operation performed by each detection element 100 according to the first embodiment. FIG. 5A illustrates a configuration example of each detection element 100. The configuration example of each detection element 100 illustrated in FIG. 5A is the same as the configuration example of the detection element 100 illustrated in FIG. 4B. Specifically, each detection element 100 includes the scintillators 101 and 102, the optical sensors 104 and 105, and the variable layer 103.

FIG. 5B illustrates the case where the incident X-rays are weak. Because pileup hardly occurs in such a case, the variable layer 103 is in the first state in which the variable layer 103 transmits scintillator light. The incident X-rays is converted into scintillator light at the position at which the incident X-rays stochastically arrive according to the intensity of the energy. When the variable layer 103 is in the first state of transmitting scintillator light, the scintillator light is movable inside a scintillator 106, and detected by the optical sensor 104 or the optical sensor 105. More specifically, the scintillator light converted by the scintillator 101 is detected by one of the optical sensor 104 and the optical sensor 105. In the same manner, the scintillator light converted by the scintillator 102 is detected by one of the optical sensor 104 and the optical sensor 105.

The output signals detected by the optical sensor 104 and the optical sensor 105 are added to be used. Specifically, scintillation light that occurs by one photon of the incident X-rays is detected by the two optical sensors 104 and 105, to increase the detection efficiency. This structure increases the photon detection efficiency, and enables data collection with reduced X-rays. Such reduction in X-ray dose enables suppression of pileup.

FIG. 5C illustrates the case where the incident X-rays are strong. For example, when the incident X-rays are strong and the variable layer 103 is in the first state of transmitting scintillator light, the optical sensor 104 can detect scintillator light converted by the scintillator 101 and scintillator light converted by the scintillator 102. In such a case, pileup may occur in the optical sensor 104 with high probability. Otherwise, when the incident X-rays are strong and the variable layer 103 is in the first state of transmitting scintillator light, the scintillator 101 may not be able to completely convert the incident X-rays into scintillator light and may cause pileup with high probability. For this reason, the switching controller 13b switches the variable layer 103 from the first state to the second state, when the intensity of the incident X-rays measured by the sensor 13c is higher than the predetermined threshold. Specifically, the variable layer 103 is switched by the switching controller 13b from the first state in which the variable layer 103 transmits scintillator light to the second state in which the variable layer 103 does not transmit scintillator light.

By the switching, the scintillator light converted by the scintillator 101 is detected by the optical sensor 104, because the scintillator light cannot pass through the variable layer 103. In addition, the scintillator light converted by the scintillator 102 is detected by the optical sensor 105, because the scintillator light cannot pass through the variable layer 103. As a result, even when pileup occurs in the optical sensor 104, no pileup occurs in the optical sensor 105, and the optical sensor 105 can be maintained at a state of being able to detect scintillator light. In addition, for example, even when scintillator 101 comes into a pileup state as illustrated in FIG. 5C, the scintillator 102 does not come into a pileup state, and can be maintained at a state of being able to convert the incident X-rays into scintillator light.

FIG. 6 is a flowchart illustrating a procedure of processing performed by the switching controller 13b according to the first embodiment. As illustrated in FIG. 6, the switching controller 13b determines whether pileup has occurred, based on the intensity of the incident X-rays measured by the sensor 13c (Step S101). When the switching controller 13b determines that no pileup has occurred (Step S101, No), the switching controller 13b repeatedly determines whether pileup has occurred.

By contrast, when the switching controller 13b determines that pileup has occurred (Step S101, Yes), the switching controller 13b determines whether the variable layer 103 is in a non-transmission state (Step S102). When the switching controller 13b determines that the variable layer 103 is in the non-transmission state (Step S102, Yes), the switching controller 13b ends the processing. By contrast, when the switching controller 13b determines that the variable layer 103 is not in the non-transmission state (Step S102, No), the switching controller 13b switches the variable layer 103 to the non-transmission state (Step S103), and ends the processing. When the switching controller 13b determines that the pileup that occurred has been removed, the switching controller 13b may switch the variable layer 103 from the second state to the first state.

As described above, according to the first embodiment, the switching controller 13b controls switching of the variable layer 103 between the first state and the second state, depending on the intensity of the incident X-rays measured by the sensor 13c. For example, when the incident X-rays are strong, the variable layer 103 is switched by the switching controller 13b from the first state in which the variable layer 103 transmits scintillator light to the second state in which the variable layer 103 does not transmit scintillator light. By the switching, for example, the scintillator light converted by the scintillator 101 is detected by the optical sensor 104, and the scintillator light converted by the scintillator 102 is detected by the optical sensor 105. As a result, even when pileup occurs in the optical sensor 104, no pileup occurs in the optical sensor 105, and the optical sensor 105 can be maintained at a state of being able to detect scintillator light. In addition, even when scintillator 101 comes into a pileup state, the scintillator 102 does not come into a pileup state, and can be maintained at a state of being able to convert the incident X-rays into scintillator light. Specifically, the first embodiment enables reduction in occurrence of counting loss of the incident X-rays.

Modification of First Embodiment

Figure 7A:
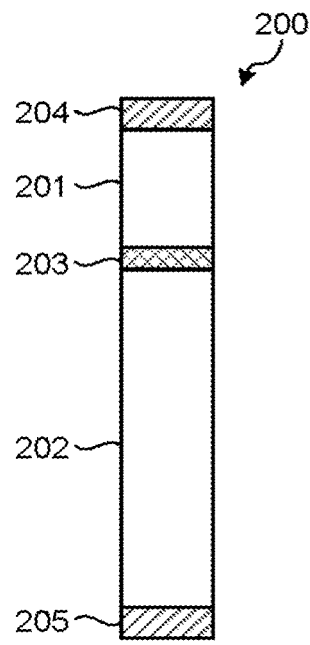
FIG. 7A is a diagram for explaining a processing operation performed by the detection element according to a modification of the first embodiment.
Figure 7B:
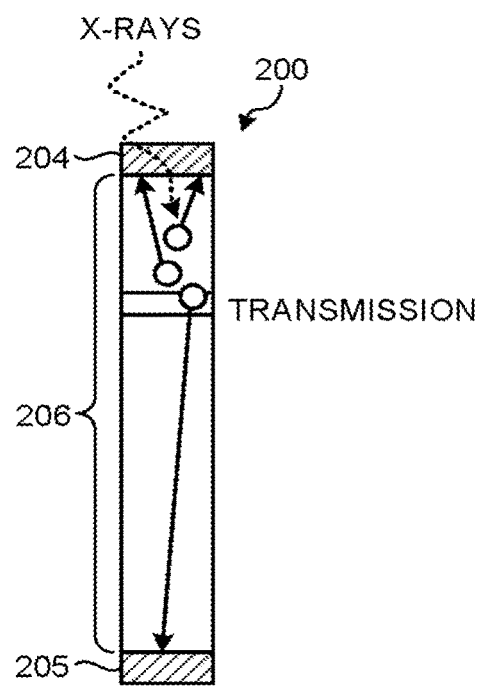
FIG. 7B is a diagram for explaining a processing operation performed by the detection element according to the modification of the first embodiment.
Figure 7C:
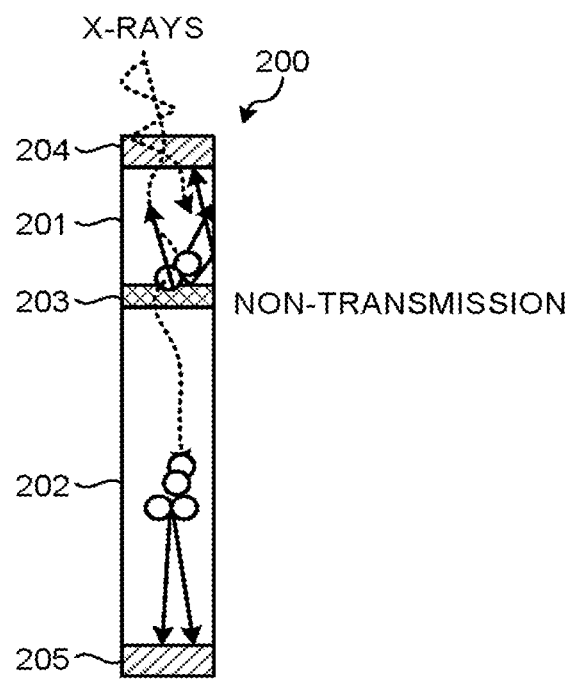
FIG. 7C is a diagram for explaining a processing operation performed by the detection element according to the modification of the first embodiment.

The first embodiment described above illustrates the case where the variable layer 103 is disposed in substantially the center of each detection element 100. However, the position where the variable layer is disposed is not limited to substantially the center of each detection element, but may be changed as desired. For example, the variable layer may be disposed in a position where X-rays with low energy band can be removed, because X-rays with low energy band may easily cause pileup and may not contribute to X-ray CT images. FIG. 7A to FIG. 7C are diagrams for explaining a processing operation performed by a detection element 200 according to a modification of the first embodiment.

For example, as illustrated in FIG. 7A, each detection element 200 according to the modification of the first embodiment includes scintillators 201 and 202, optical sensors 204 and 205, and a variable layer 203. Each of the scintillators 201 and 202 converts incident X-rays radiated from the X-ray source into scintillator light. The optical sensors 204 and 205 are SiPMs, and detect the scintillator light converted by the scintillators 201 and 202.

The variable layer 203 is provided in the scintillators 201 and 202, and switchable between the first state in which the variable layer 203 transmits scintillator light and the second state in which the variable layer 203 does not transmit scintillator light. The variable layer 203 is disposed to be shifted from the center toward the optical sensor 204 in the detection element 200. The arrival position of incident X-rays has an increased length in the depth direction of the scintillator with higher probability in accordance with the intensity of the energy. For this reason, the position where the variable layer 203 is disposed corresponds to a position at which X-rays with low energy band that do not contribute to X-ray CT images arrive with high probability. With this structure, the variable layer 203 is capable of dividing X-rays into X-rays with low energy band that do not contribute to X-ray CT images, and X-rays with an energy band used for reconstructing X-ray CT images, when the variable layer 203 is switched to the second state in which the variable layer 203 does not transmit scintillator light. The first state and the second state of the variable layer 203 can be controlled as desired for each of the individual detection elements. In the following explanation, suppose that the variable layer 203 is in the first state in which the variable layer 203 transmits scintillator light at the start of imaging performed by the X-ray CT apparatus, for the sake of convenience of explanation.

FIG. 7B illustrates the case where the incident X-rays are weak. Because pileup hardly occurs in such a case, the variable layer 203 is in the first state in which the variable layer 203 transmits scintillator light. The incident X-rays are converted into scintillator light at the position at which the incident X-rays stochastically arrive according to the intensity of the energy. When the variable layer 203 is in the first state of transmitting scintillator light, the scintillator light is movable inside a scintillator 206, and detected by the optical sensor 204 or the optical sensor 205. More specifically, the scintillator light converted by the scintillator 201 is detected by one of the optical sensor 204 and the optical sensor 205. In the same manner, the scintillator light converted by the scintillator 202 is detected by one of the optical sensor 204 and the optical sensor 205.

The output signals detected by the optical sensor 204 and the optical sensor 205 are added to be used. Specifically, scintillation light that occurs by one photon of the incident X-rays is detected by the two optical sensors 204 and 205, to increase the detection efficiency. This structure increases the photon detection efficiency, and enables data collection with reduced X-rays. Such reduction in X-ray dose enables suppression of pileup.

FIG. 7C illustrates the case where the incident X-rays are strong. For example, when the incident. X-rays are strong and the variable layer 203 is in the first state of transmitting scintillator light, the optical sensor 204 can detect scintillator light converted by the scintillator 201 and scintillator light converted by the scintillator 202. In such a case, pileup may occur in the optical sensor 204 with high probability. Otherwise, when the incident X-rays are strong and the variable layer 203 is in the first state of transmitting scintillator light, the scintillates 201 may not be able to completely convert the incident X-rays into scintillator light and may cause pileup with high probability. For this reason, the switching controller 13b switches the variable layer 203 from the first state to the second state, when the intensity of the incident X-rays measured by the sensor 13c is higher than the predetermined threshold. Specifically, the variable layer 203 is switched by the switching controller 13b from the first state in which the variable layer 203 transmits scintillator light to the second state in which the variable layer 203 does not transmit scintillator light.

By the switching, the scintillator light converted by the scintillator 201 is detected by the optical sensor 204, because the scintillator light cannot pass through the variable layer 203. In addition, the scintillator light converted by the scintillator 202 is detected by the optical sensor 205, because the scintillator light cannot pass through the variable layer 203. As a result, even when pileup occurs in the optical sensor 204, no pileup occurs in the optical sensor 205, and the optical sensor 205 can be maintained at a state of being able to detect scintillator light. In addition, for example, even when scintillator 201 comes into a pileup state as illustrated in FIG. 7C, the scintillator 202 does not come into a pileup state, and can be maintained at a state of being able to convert the incident X-rays into scintillator light.

Although the switching controller 13b has been explained with the structure of including the sensor 13c that measures the intensity of the incident X-rays, the switching controller 13b may not include the sensor 13c. In such a case, the switching controller 13b acquires a counting result by, for example, the collector 14, determines the intensity of the incident X-rays based on the acquired counting result, and controls switching of the variable layer 103 (203) between the first state and the second state. For example, the switching controller 13b switches the variable layer to the second state, when the counting result is equal to or higher than the predetermined threshold. As described above, the switching controller 13b switches the variable layer 103 (203) to the second state, when the intensity of the signal detected by the sensor 13c or the detection element 100 (200) of the detector 13 in imaging is equal to or higher than the predetermined threshold.

Although the switching controller 13b has been explained with the structure of controlling switching of the variable layer 103 between the first state and the second state by measuring the intensity of the incident X-rays in imaging, the embodiments are not limited to this. The switching controller 13b may control switching of the variable layer 103 between the first state and the second state based on preset imaging conditions. For example, the switching controller switches the variable layer 103 to the second state, when a set value that is set as an imaging condition is equal to or higher than the predetermined threshold. Specifically, the switching controller 13b switches the variable layer 103 to the second state, when X-ray irradiation parameters such as a tube voltage and a tube current are equal to or higher than the predetermined thresholds.

Although the switching controller 13b has been explained with the structure of controlling switching of the variable layer 103 between the first state and the second state, depending on the intensity of the incident X-rays, the embodiments are not limited to this. For example, the switching controller 13b may control switching of the variable layer 103 between the first state and the second state, in accordance with the energy band of the incident X-rays. For example, the switching controller 13b performs control to switch the variable layer 103 between the first state and the second state, when the upper limit of the energy band of the emitted X-rays determined based on the imaging conditions is equal to or higher than the predetermined threshold. More specifically, the switching controller 13b switches the variable layer 103 to the second state, when the upper limit of the energy band of the emitted X-rays determined according to the tube voltage is equal to or higher than the predetermined threshold, because the incident X-ray dose with high energy band may be large.

In addition, the switching controller 13b may switch the variable layer 103 to the second state, when the number of counts of signals having an energy band equal to or larger than a predetermined energy value among signals detected by the detector 13 is equal to or higher than the predetermined threshold. Although the upper limit of the energy of the detected X-ray photon serves as the upper limit of the energy of the irradiation X-rays, when a plurality of X-ray photons are simultaneously made incident within a short time, the output pulses overlap each other, and the incident X-ray photons may be erroneously detected as one incident X-ray photon having higher energy than the original. In other words, when an X-ray photon that exceeds the upper limit of the energy of the irradiation X-rays is detected, the detection can be regarded as erroneous detection caused by pileup. In view of the above, when the signals detected by the detector 13 are analyzed to switch the variable layer 103 to the second state, the variable layer 103 may be switched to the second state, by determining that pileup occurs, when an X-ray having an energy higher than the upper limit of the spectrum of the irradiation X-rays determined by the preset tube voltage is detected.

The X-ray CT apparatus can collect scintillator light of different energy bands converted by the respective scintillators that are partitioned by the variable layer, by switching the state of the variable layer to the second state when the incident X-rays are weak. This structure enables generation of X-ray CT images for discrimination of energies.

Second Embodiment

The first embodiment illustrates the case where one variable layer is disposed in the scintillator. A plurality of variable layers may be disposed in the scintillator. A second embodiment illustrates the case where a plurality of variable layers are provided in a scintillator.

The X-ray CT apparatus according to the second embodiment has the same configuration as the configuration of the X-ray CT apparatus illustrated in FIG. 1, except that the structure of the detection elements included in the detector 13 and part of the function of the switching controller 13b are different. For this reason, the following explanation illustrates only the structure of each detection element 300 according to the second embodiment, and the function of the switching controller 13b according to the second embodiment. FIG. 8A to FIG. 8D are diagrams for explaining each detection element 300 according to the second embodiment.

Figure 8A:
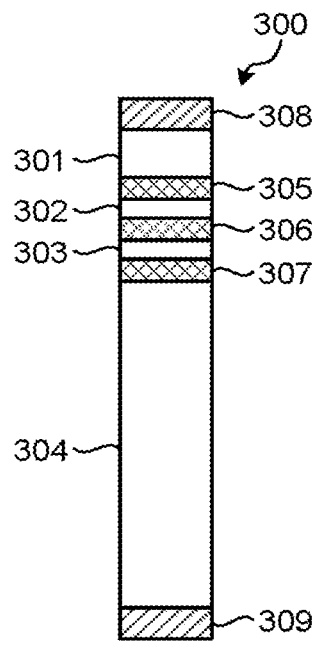
FIG. 8A is a diagram for explaining a detection element according to a second embodiment.

Each detection element 300 according to the second embodiment further includes a variable layer in at least one of the first region and the second region in the scintillator. For example, as illustrated in FIG. 8A, each detection element 300 according to the second embodiment includes scintillators 301, 302, 303, and 304, optical sensors 308 and 309, and variable layers 305, 306, and 307. Each of the scintillators 301, 302, 303, and 304 converts the incident X-rays radiated from the X-ray source into scintillator light. The explanation is made on the supposition that, for example, the scintillators 301 and 302 serve as the first region close to X-ray source, and the scintillators 303 and 304 serve as the second region distant from the X-ray source. The scintillator 301 may serve as the first region close to the X-ray source, and the scintillators 302, 303, and 304 may serve as the second region distant from the X-ray source. Otherwise, the scintillators 301, 332, and 303 may serve as the first region close to the X-ray source, and the scintillator 304 may serve as the second region distant from the X-ray source. The optical sensors 308 and 309 are SiPMs, and detect scintillator light converted by the scintillators 301, 302, and 303.

The variable layers 305, 306, and 307 are provided in the scintillators 301, 302, 303, and 304, and each of the variable layers is switchable between the first state in which the variable layer transmits scintillator light and the second state in which the variable layer does not transmit scintillator light. In other words, the variable layer 306 is a variable layer that is switchable between the first state in which the variable layer 306 transmits scintillator light between the first region (scintillators 301 and 302) and the second region (scintillators 303 and 304) and the second state in which the variable layer 306 does not transmit scintillator light between the first region and the second region. The variable layer 305 is a variable layer that is further provided in the first region (between the scintillators 301 and 302) in the scintillator. The variable layer 307 is a variable layer that is further provided in the second region (between the scintillators 303 and 304) in the scintillator. The variable layers 305, 306, and 307 are arranged in respective positions that are shifted from substantially the center of the detection element 300 toward the optical sensor 308 in the detection element 300. These positions are positions at which X-rays with low energy band that do not contribute to X-ray CT images arrive with high probability. More specifically, the energy of X-rays that arrive at the position where the variable layer 305 is disposed is smaller than the energy of X-rays that arrive at the position where the variable layer 306 is disposed, and the energy of X-rays that arrive at the position where the variable layer 306 is disposed is smaller than the energy of X-rays that arrive at the position where the variable layer 307 is disposed. The variable layers 305, 306, and 307 arranged as described above enable division of X-rays with low energy band that do not contribute to X-ray CT images, and X-rays of the energy band used for reconstructing X-ray CT images into multiple levels. The first state and the second state of each of the variable layers 305, 306, and 307 can be controlled as desired for each of the individual detection elements. In the following explanation, suppose that the variable layers 305, 306, and 307 are in the first state in which the variable layers transmit scintillator light at the start of imaging performed by the X-ray CT apparatus, for the sake of convenience of explanation.

The switching controller 13b according to the second embodiment switches each of the variable layers 305 to 307 from the first state to the second state, depending on the intensity of the incident X-rays. For example, the switching controller 13b according to the second embodiment acquires the counting result obtained by the optical sensor 309 from the collector 14, to determine the intensity of the incident X-rays, and control switching of each of the variable layers 305 to 307 between the first state and the second state based on the determined intensity of the incident X-rays.

For example, when the incident X-rays are weak, the switching controller 13b sets each of the variable layers 305, 306, and 307 to the first state in which the variable layer transmits scintillator light. In such a case, scintillator light converted by the scintillators 301, 302, 303, and 304 are detected by either of the optical sensors 308 and 309.

Figure 8B:
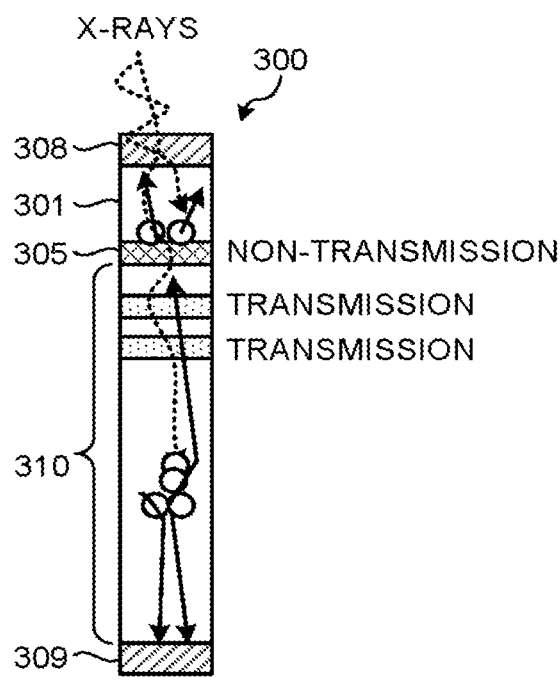
FIG. 8B is a diagram for explaining the detection element according to the second embodiment.

When the switching controller 13b determines that the intensity of the incident X-rays is equal to or higher than the predetermined threshold the case where all the variable layers 305, 306, and 307 are in the first state of transmitting scintillator light, the switching controller 13b switches the variable layer 305 to the second state, as illustrated in FIG. 8B. Specifically, the switching controller 13b selects the variable layer 305 having the minimum energy band, and switches the selected variable layer 305 to the non-transmission state, when the switching controller 13b determines that the intensity of the incident X-rays is equal to or higher than the predetermined threshold and none of the variable layers 305, 306, and 307 are in the non-transmission state.

By the switching, the scintillator light converted by the scintillator 301 is detected by the optical sensor 308, because the scintillator light cannot pass through the variable layer 305. In addition, when the scintillators 302, 303, and 304 are referred to as scintillator 310, the scintillator light converted by the scintillator 310 is detected by the optical sensor 309, because the scintillator light cannot pass through the variable layer 305. As a result, no pileup occurs in the optical sensor 309, and the optical sensor 309 can be maintained at a state of being able to detect scintillator light. In addition, for example, even when scintillator 301 comes into a pileup state as illustrated in FIG. 8B, the scintillator 310 does not come into a pileup state, and can be maintained at a state of being able to convert the incident X-rays into scintillator light.

Figure 8C:
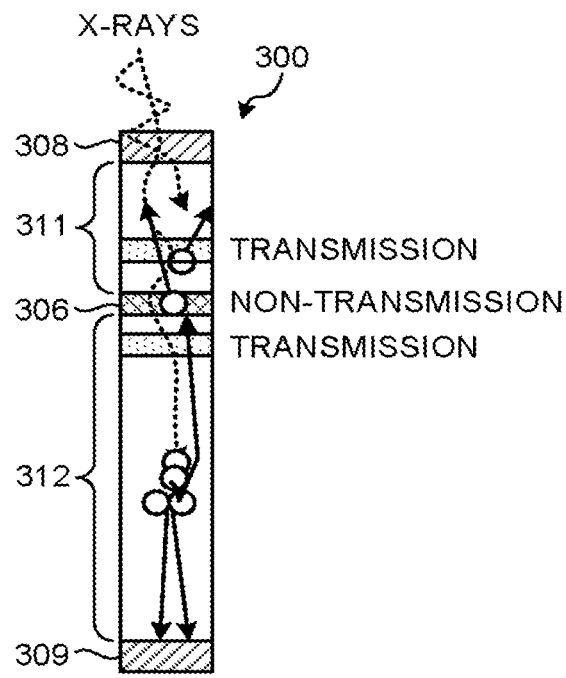
FIG. 8C is a diagram for explaining the detection element according to the second embodiment.

Thereafter, when the switching controller 13b determines that the intensity of the incident X-rays is equal to or higher than the predetermined threshold after switching the variable layer 305 to the first state, the switching controller 13b switches the variable layer 306 to the second state, as illustrated in FIG. 8C. Specifically, the switching controller 13b selects the variable layer 306 having an energy band higher by one than that of the variable layer 305 in the non-transmission state, and switches the selected variable layer 306 to the non-transmission state, when the switching controller 13b determines that the intensity of the incident X-rays is equal to or higher than the predetermined threshold and any of the variable layers is in the non-transmission state.

When the scintillators 301 and 302 are referred to as scintillator 311 and the scintillators 303 and 304 are referred to as scintillator 312, the scintillator light converted by the scintillator 311 is detected by the optical sensor 308, because the scintillator light cannot pass through the variable layer 306. In addition, the scintillator light converted by the scintillator 312 is detected by the optical sensor 309, because the scintillator light cannot pass through the variable layer 306. As a result, no pileup occurs in the optical sensor 309, and the optical sensor 309 can be maintained at a state of being able to detect scintillator light. In addition, for example, even when scintillator 311 comes into a pileup state as illustrated in FIG. 8C, the scintillator 312 does not come into a pileup state, and can be maintained at a state of being able to convert the incident X-rays into scintillator light.

Figure 8D:
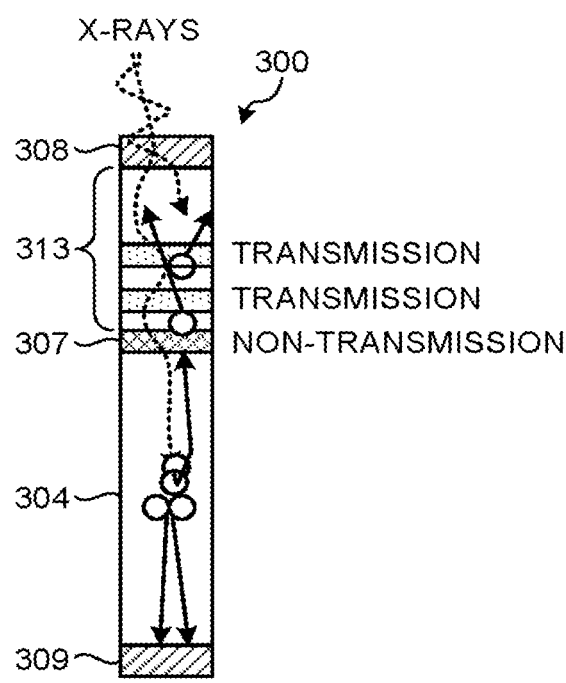
FIG. 8D is a diagram for explaining the detection element according to the second embodiment.

Thereafter, when the switching controller 13b determines that the intensity of the incident X-rays is equal to or higher than the predetermined threshold after switching the variable layer 306 to the first state, the switching controller 13b switches the variable layer 307 to the second state, as illustrated in FIG. 8D. Specifically, the switching controller 13b selects the variable layer 307 having an energy band higher by one than that of the variable layer 306 in the non-transmission state, and switches the selected variable layer 307 to the non-transmission state, when the switching controller 13b determines that the intensity of the incident. X-rays is equal to or higher than the predetermined threshold and any of the variable layers is in the non-transmission state.

When the scintillators 301, 302, and 303 are referred to as scintillator 313, the scintillator light converted by the scintillator 313 is detected by the optical sensor 308, because the scintillator light cannot pass through the variable layer 307. In addition, the scintillator light converted by the scintillator 304 is detected by the optical sensor 309, because the scintillator light cannot pass through the variable layer 307. As a result, no pileup occurs in the optical sensor 309, and the optical sensor 309 can be maintained at a state being able to detect scintillator light. In addition, for example, even when scintillator 313 comes into a pileup state as illustrated in FIG. 8D, the scintillator 304 does not come into a pileup state, and can be maintained at a state of being able to convert the incident X-rays into scintillator light.

Figure 9:
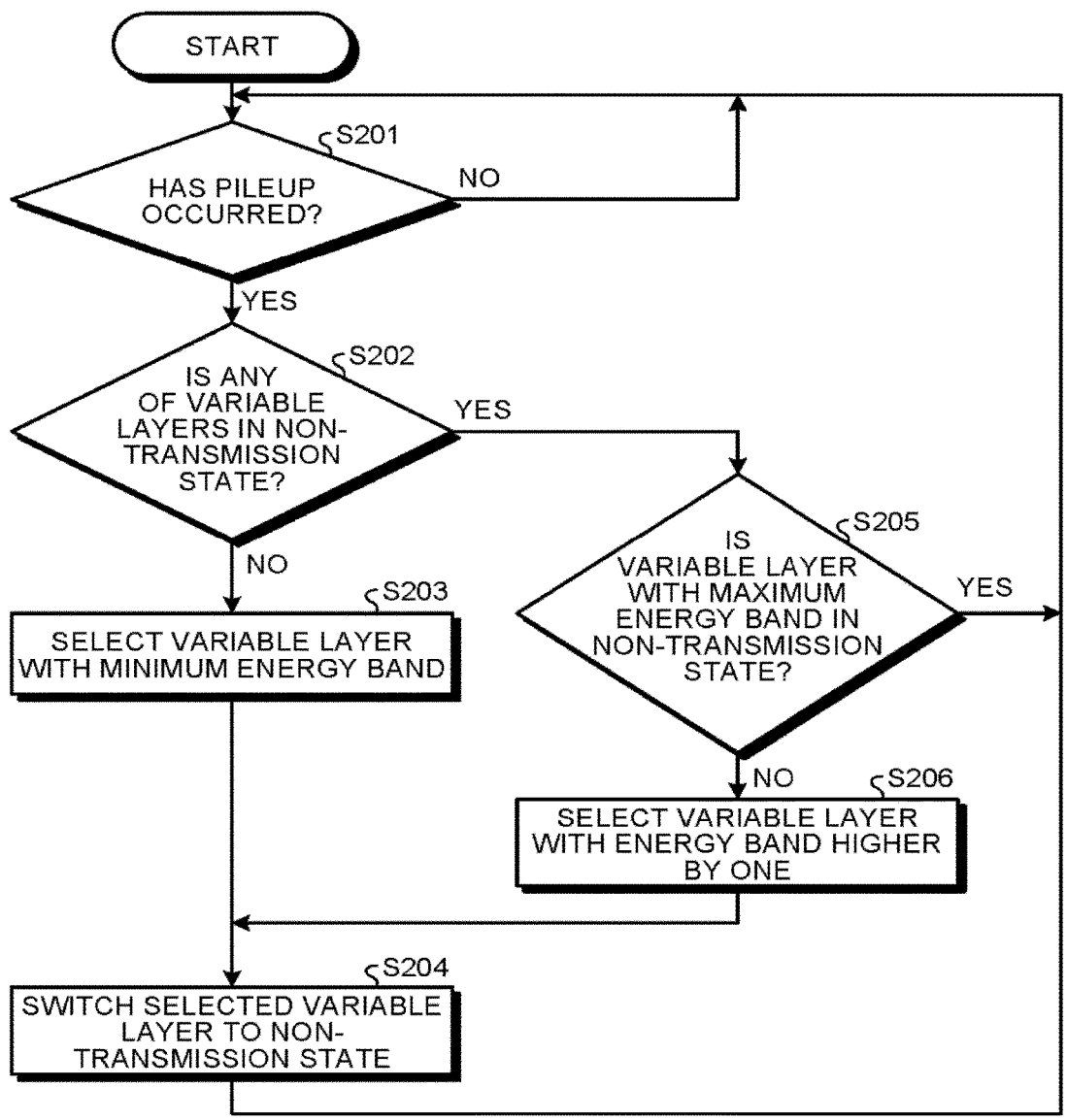
FIG. 9 is a flowchart illustrating a procedure of processing performed by the switching controller according to the second embodiment.

FIG. 9 is a flowchart illustrating a procedure of processing performed by the switching controller 13b according to the second embodiment. As illustrated in FIG. 9, the switching controller 13b according to the second embodiment determines whether pileup has occurred, based on the intensity of the incident X-rays measured by the sensor 13c (Step S201). For example, the switching controller 13b acquires the counting result obtained by the optical sensor 309 from the collector 14, to determine whether the intensity of the incident X-rays is equal to or higher than the predetermined threshold. The switching controller 13b determines that pileup has occurred, when the intensity of the incident X-rays is equal to or higher than the predetermined threshold. When the switching controller 13b determines that no pileup has occurred (Step S201, No), the switching controller 13b repeatedly determines whether pileup has occurred.

By contrast, when the switching controller 13b determines that pileup has occurred (Step S201, Yes), the switching controller 13b determines whether any of the variable layers is in a non-transmission state (Step S202). When the switching controller 13b determines that none of the variable layers are in the non-transmission state (Step S202, No), the switching controller 13b selects a variable layer with the minimum energy band (Step S203). Thereafter, the switching controller 13b switches the selected variable layer to the non-transmission state (Step S204), and goes to Step S201.

By contrast, when the switching controller 13b determines that any of the variable layers is in the non-transmission state (Step S202, Yes), the switching controller 13b determines whether the variable layer with the maximum energy band is in the non-transmission state (Step S205). When the switching controller 13b determines that the variable layer with the maximum energy band is in the non-transmission state (Step S205, Yes), the switching controller 13b goes to Step S201.

By contrast, when the switching controller 13b determines that the variable layer with the maximum energy band is not in the non-transmission state (Step S205, No), the switching controller 13b selects a variable layer having an energy band higher by one (Step S206), and goes to Step S204.

As described above, the second embodiment divides the incident X-rays with low energy band that do not contribute to X-ray CT images and the incident X-rays with an energy band used for reconstructing X-ray CT images into multiple levels, according to the intensity of the incident X-rays. With this structure, the second embodiment enables reduction in occurrence of counting loss of X-rays.

Although the switching controller 13b has been explained with the structure of acquiring the counting result obtained by the optical sensor 309 from the collector 14, determining the intensity of the incident X-rays, and controlling switching of each of the variable layers 305 to 307 between the first state and the second state based on the determined intensity of the incident X-rays, the embodiments are not limited to this. For example, the switching controller 13b may set a plurality of thresholds for the intensity of the incident X-rays, and include association information in which the set thresholds are associated with the respective variable layers. In such a case, when the intensity of the signal detected by the detector 13 exceeds one of the thresholds that are set for the intensity of the signal, the switching controller 13b refers to the association information, to specify the variable layer that is associated with the threshold having the highest value among the thresholds that the intensity of the signal exceeds. The switching controller 13b thereafter switches the specified variable layer to the second state.

Although the switching controller 13b has been explained with the structure of controlling switching of each of the variable layers 305 to 307 between the first state and the second state by measuring the incident X-ray intensity during application of X-rays, the embodiments are not limited to this. For example, the switching controller 13b may control switching of each of the variable layers 305 to 307 between the first state and the second state based on preset imaging conditions. Specifically, the switching controller 13b may set a plurality of thresholds for X-ray irradiation parameters such as the tube voltage and the tube current, and include association information in which the set thresholds are associated with the respective variable layers. When the set value of the X-ray irradiation parameters such as the tube voltage and the tube current set as the imaging conditions exceeds one of the thresholds that are set for the imaging conditions, the switching controller 13b refers to the association information, to specify the variable layer that is associated with the threshold having the highest value among the thresholds that the set value exceeds. The switching controller 13b thereafter switches the specified variable layer to the second state.

Third Embodiment

A third embodiment illustrates the case of application to an area detector. The transmitted X-ray dose differs according to the thickness and density of the subject. For this reason, the incident X-rays is hardly attenuated in a thin portion of the subject or a region with a small density, and pileup easily occurs because excessive X-rays are easily made incident. In view of the above, the third embodiment illustrates the case of setting the variable layer disposed on the small energy side to a non-transmission state for region in which pileup easily occurs, and setting the variable layer disposed on the small energy side to the non-transmission state for a region in which pileup hardly occurs.

The X-ray CT apparatus according to the third embodiment has the same configuration as the configuration of the X-ray CT apparatus illustrated in FIG. 1, except that the structure of the detection elements included in the detector 13 and part of the function of the switching controller 13b are different. For this reason, the following explanation illustrates only the structure of each detection element 400 according to the third embodiment, and the function of the switching controller 13b according to the third embodiment. FIG. 10A to FIG. 10E are diagrams or explaining each detection element 400 according to the third embodiment.

Figure 10A:
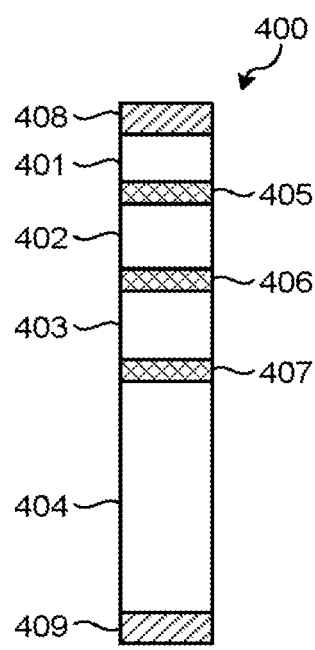
FIG. 10A is a diagram for explaining a detection element according to a third embodiment.

For example, as illustrated in FIG. 10A, each detection element 400 according to the third embodiment includes scintillators 401, 402, 403, and 404, optical sensors 408 and 409, and variable layers 405, 406, and 407. Each of the scintillators 401, 402, 403, and 404 converts the incident X-rays radiated from the X-ray source into scintillator light. The explanation is made on the supposition that, for example, the scintillators 401 and 402 serve as the first region close to the X-ray source, and the scintillators 403 and 404 serve as the second region distant from the X-ray source. The scintillator 401 may serve as the first region close to the X-ray source, and the scintillators 402, 403, and 404 may serve as the second region distant from the X-ray source. Otherwise, the scintillators 401, 402, and 403 may serve as the first region close to the X-ray source, and the scintillator 404 may serve as the second region distant from the X-ray source. The optical sensors 408 and 409 are SiPMs, and detect scintillator light converted by the scintillators 401, 402, and 403.

The variable layers 405, 406, and 407 are provided in the scintillators 401, 402, 403, and 404, and each of the variable layers is switchable between the first state in which the variable layer transmits scintillator light and the second state in which the variable layer does not transmit scintillator light. In other words, the variable layer 406 is a variable layer that is switchable between the first state in which the variable layer 406 transmits scintillator light between the first region (scintillators 401 and 402) and the second region (scintillators 403 and 404) and the second state in which the variable layer 406 does not transmit scintillator light between the first region and the second region. The variable layer 405 is a variable layer that is further provided in the first region (between the scintillators 401 and 402) in the scintillator. The variable layer 407 is a variable layer that is further provided in the second region (between the scintillators 403 and 404) in the scintillator. The variable layers 405, 406, and 407 are arranged in respective positions that are shifted from substantially the center of the detection element 400 toward the optical sensor 408 in the detection element 400. These positions are positions at which X-rays with low energy band that do not contribute to X-ray CT images arrive with high probability. More specifically, the energy of X-rays that arrive at the position where the variable layer 405 is disposed is smaller than the energy of X-rays that arrive at the position where the variable layer 406 is disposed, and the energy of X-rays that arrive at the position where the variable layer 406 is disposed is smaller than the energy of X-rays that arrive at the position where the variable layer 407 is disposed. The variable layers 405, 406, and 407 arranged as described above enable division of X-rays with low energy band that do not contribute to X-ray CT images, and X-rays of the energy band used for reconstructing X-ray CT images into multiple levels. The first state and the second state of each of the variable layers 405, 406, and 407 can be controlled as desired for each of the individual detection elements. In the following explanation, suppose that the variable layers 405, 406, and 407 are in the first tae in which the variable layers transmit scintillator light at the start of imaging performed by the X-ray CT apparatus, for the sake of convenience of explanation.

The switching controller 13b according to the third embodiment controls switching of each of the variable layers 405 to 407 between the first state and the second state, in accordance with the intensity of the incident X-rays. For example, the switching controller 13b according to the third embodiment determines the thickness and the density of the subject in pixels on a scanogram corresponding to the detection element, and estimates the intensity of the incident X-rays in the detection element. In other words, the switching controller 13b classifies the intensities of the incident X-ray based on the scanogram, and specifies the variable layer with reference to association information in which the respective classified intensities of the incident X-rays are associated with the respective variable layers. The switching controller 13b Thereafter switches the specified variable layer to the second state.

Figure 10B:
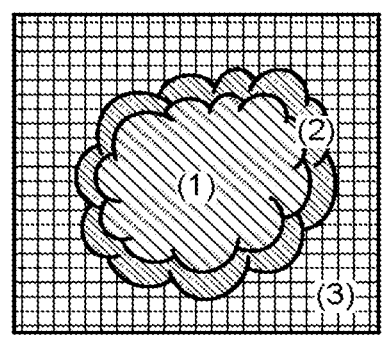
FIG. 10B is a diagram for explaining the detection element according to the third embodiment.
Figure 10C:
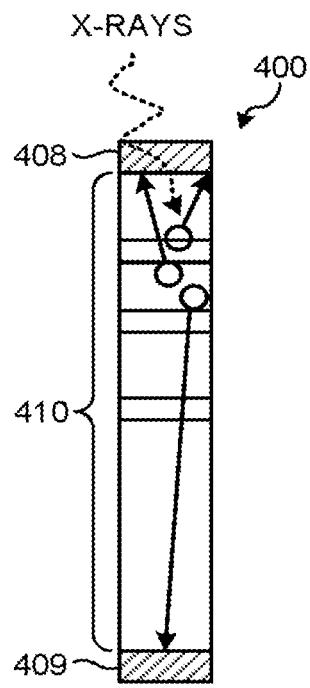
FIG. 10C is a diagram for explaining the detection element according to the third embodiment.

FIG. 10B illustrates a scanogram at a tube phase α1. In the example illustrated in FIG. 10B, pixels in the scanogram are divided into three regions of Region (1) to Region (3). The Region (1) indicates a region in which the subject has a large thickness and a high density. In the Region (1), the X-rays made incident on the detection element has small intensity. The Region (2) indicates a region in which the subject has a medium thickness and a medium density. In the Region (2), the X-rays made incident on the detection element has medium intensity. The Region (3) indicates a region in which the subject has a small thickness and a low density. In the Region (3), the X-rays made incident on the detection element has large intensity. As described above, the switching controller 13b determines the thickness and the density of the subject in pixels on the scanogram corresponding to the detection element, and estimates the intensity of the incident X-rays in the detection element.

The switching controller 13b controls switching of each of the variable layers 405 to 407 between the first state and the second state, based on the estimated intensity of the incident X-rays. FIG. 102 illustrates switching of the variable layers in the Region (1). The switching controller 13b estimates that the incident X-rays in the Region (1) is weak, and switches each of the variable layers 405, 406, and 407 to the first state of transmitting scintillator light. In such a case, when the scintillators 401, 402, 403, and 404 are referred to as scintillator 410, the scintillator light converted by the scintillator 410 is detected by either of the optical sensor 408 and the optical sensor 409.

Figure 10D:
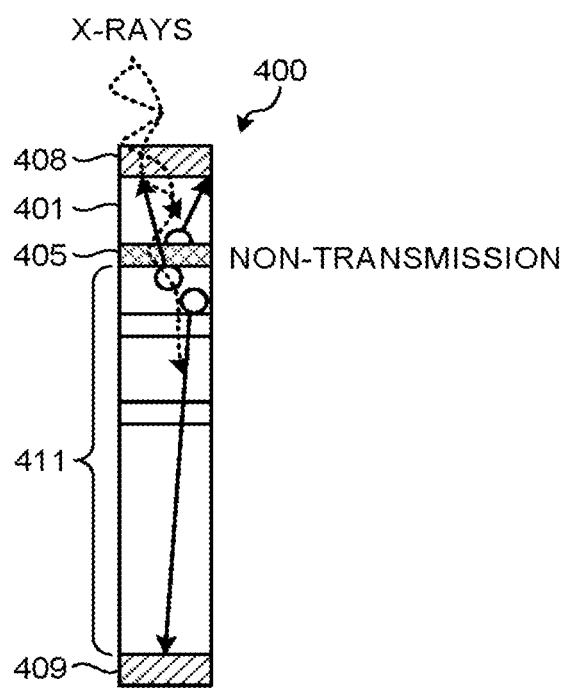
FIG. 10D is a diagram for explaining the detection element according to the third embodiment.

FIG. 10D illustrates switching of the variable layers in the Region (2). The switching controller 13b estimates that the incident X-rays in the Region is medium, and switches the variable layer 405 to the second state. In such a case, the scintillator light converted by the scintillator 401 is detected by the optical sensor 408, because the scintillator light cannot pass through the variable layer 405. In addition, when the scintillators 402, 403, and 404 are referred to as scintillator 411, the scintillator light converted by the scintillator 411 is detected by the optical sensor 409, because the scintillator light cannot pass through the variable layer 405.

Figure 10E:
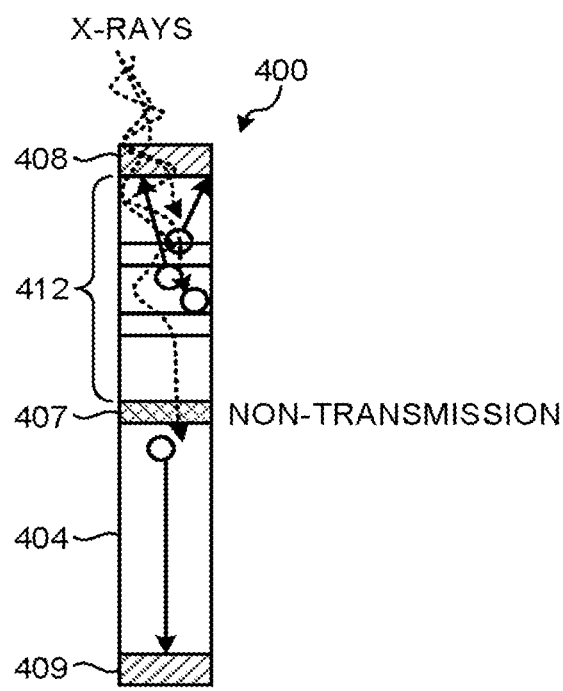
FIG. 10E is a diagram for explaining the detection element according to the third embodiment.

FIG. 10E illustrates switching of the variable layers in the Region (3). The switching controller 13b estimates that the incident X-rays in the Region (3) is strong, and switches the variable layer 407 to the second state. In such a case, when the scintillators 401, 402, and 403 are referred to as scintillator 412, the scintillator light converted by the scintillator 412 is detected by the optical sensor 408, because the scintillator light cannot pass through the variable layer 407. In addition, the scintillator light converted by the scintillator 404 is detected by the optical sensor 409, because the scintillator light cannot pass through the variable layer 407.

Figure 11:
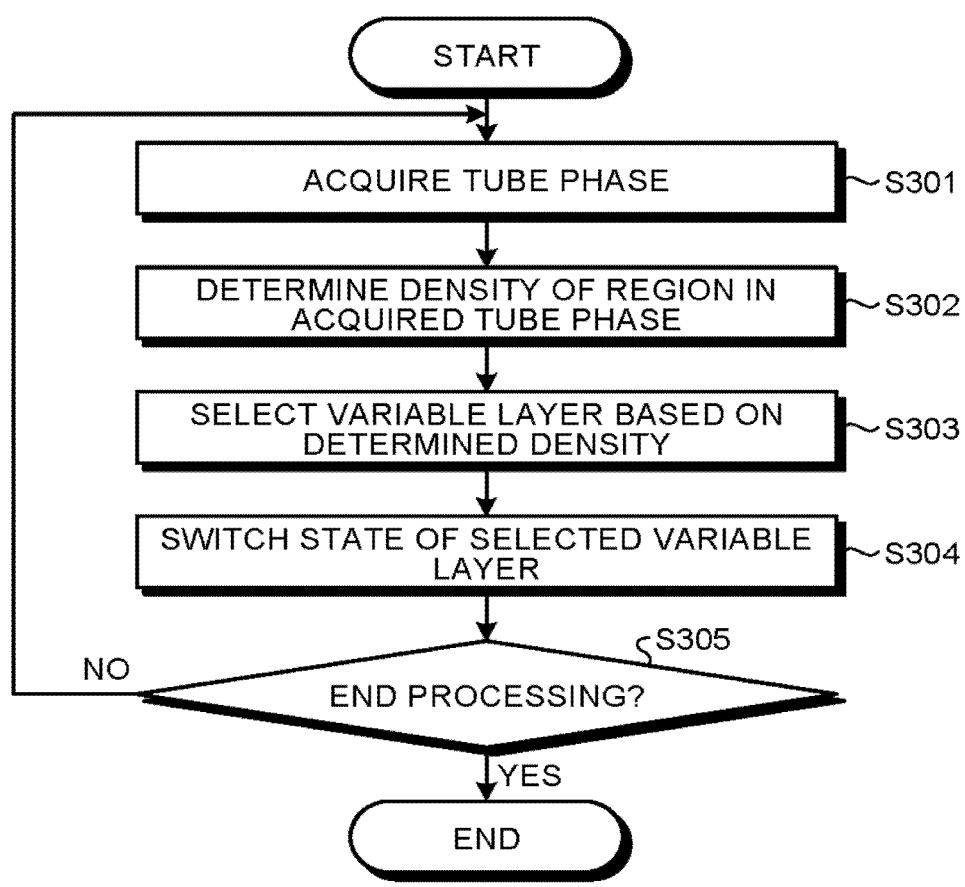
FIG. 11 is a flowchart illustrating a procedure of processing performed by the switching controller according to the third embodiment.

FIG. 11 is a flowchart illustrating a procedure of processing performed by the switching controller 13b according to the third embodiment. As illustrated in FIG. 11, the switching controller 13b acquires the tube phase (Step S301). The switching controller 13b thereafter determines the density of the region in the acquired tube phase (Step S302). Thereafter, the switching controller 13b selects the variable layer based on the determined density (Step S303). The switching controller 13b switches the state of the selected variable layer (Step S304). Thereafter, the switching controller 13b determines whether to end the processing (Step S305). When the switching controller 13b determines not to end the processing (Step S305, No), the switching controller 13b goes to Step S301. By contrast, when the switching controller 13b determines to end the processing (Step S305, Yes), the switching controller 13b ends the processing.

As described above, the structure of the third embodiment determines the thickness and the density of the subject in pixels on the scanogram, to estimate the intensity of the incident X-rays in the detection element. The structure divides X-rays with low energy band that do not contribute to X-ray CT images, and X-rays of the energy band used for reconstructing X-ray CT images into multiple levels, according to the estimated intensity of the incident X-rays. With this structure, the third embodiment enables reduction in occurrence of counting loss of X-rays.

Fourth Embodiment

A fourth embodiment illustrates the case of controlling switching of each of the variable layers between the first state and the second state in accordance with the energy band of X-rays to be detected. For example, energy discrimination is performed based on the output of the scintillator by dividing a low energy band side from a high energy band side with the variable layer interposed therebetween.

The X-ray CT apparatus according to the fourth embodiment has the same configuration as the configuration of the X-ray CT apparatus illustrated in FIG. 1, except that the structure of the detection elements included in the detector 13 and part of the function of the switching controller 13b are different. For this reason, the following explanation illustrates only the structure of each detection element 500 according to the fourth embodiment, and the function of the switching controller 13b according to the fourth embodiment. FIG. 12A to FIG. 12D are diagrams for explaining each detection element 500 according to the fourth embodiment.

Figure 12A:
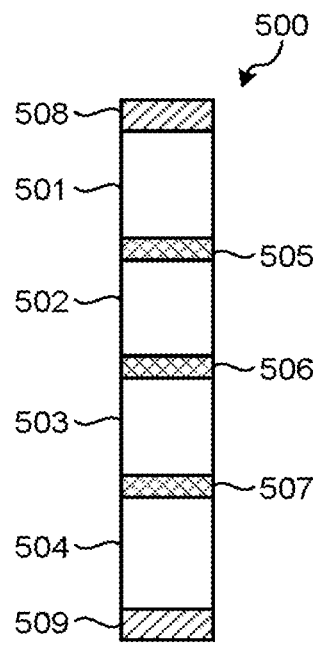
FIG. 12A is a diagram for explaining a detection element according to a fourth embodiment.

For example, as illustrated in FIG. 12A, each detection element 500 according to the fourth embodiment includes scintillators 501, 502, 503, and 504, optical sensors 508 and 509, and variable layers 505, 506, and 507. Each of the scintillators 501, 502, 503, and 504 converts the incident X-rays radiated from the X-ray source into scintillator light. The explanation is made on the supposition that, for example, the scintillators 501 and 502 serve as the first region close to the X-ray source, and the scintillators 503 and 504 serve as the second region distant from the X-ray source. The scintillator 501 may serve as the first region close to the X-ray source, and the scintillators 502, 503, and 504 may serve as the second region distant from the X-ray source. Otherwise, the scintillators 501, 502, and 503 may serve as the first region close to the X-ray source, and the scintillator 504 may serve as the second region distant from the X-ray source. The optical sensors 508 and 509 are SiPMs, and detect scintillator light converted by the scintillators 501, 502, 503, and 504.

The variable layers 505, 506, and 507 are provided in the scintillators 501, 502, 503, and 504, and each of the variable layers is switchable between the first state in which the variable layer transmits scintillator light and the second state in which the variable layer does not transmit scintillator light. In other words, the variable layer 506 is a variable layer that is switchable between the first state in which the variable layer 506 transmits scintillator light between the first region (scintillators 501 and 502) and the second region (scintillators 503 and 504) and the second state in which the variable layer 506 does not transmit scintillator light between the first region and the second region. The variable layer 505 is a variable layer that is further provided in the first region (between the scintillators 501 and 502) in the scintillator. The variable layer 507 is a variable layer that is further provided in the second region (between the scintillators 503 and 504) in the scintillator. The variable layers 505, 506, and 507 are arranged in respective positions such that the variable layers are arranged at substantially equal intervals in the detection element 500. The energy of the incident X-rays that arrive at the position where the variable layer 505 is disposed has low energy with high probability, the energy of the incident X-rays that arrive at the position where the variable layer 506 is disposed has medium energy with high probability, and the energy of the incident X-rays that arrive at the position where the variable layer 507 is disposed has high energy with high probability. The variable layers 505, 506, and 507 arranged as described above enable collection of scintillator light divided by the energy band of the incident X-rays. The first state and the second state of each of the variable layers 505, 506, and 507 can be controlled as desired for each of the individual detection elements. In the following explanation, suppose that the variable layers 505, 506, and 507 are in the first state in which the variable layers transmit scintillator light at the start of imaging performed by the X-ray CT apparatus, for the sake of convenience of explanation.

The switching controller 13b according to the fourth embodiment controls switching of each of the variable layers between the first state and the second state, in accordance with the energy band of the X-rays to be detected. For example, when the system controller 38 receives an instruction to collect scintillator light divided by energy band from the operator through the input device 31, the system controller 38 instructs the switching controller 13b of the detector 13 to switch each of the variable layers between the first state and the second state, through the scan controller 33. The input device 31 is also referred to as receiving unit. Specifically, the receiving unit receives setting of energy band of the X-rays to be collected. The switching controller 13b control switching of each of the variable layers between the first state and the second state, in accordance with the energy band, the setting of which has been received by the receiving unit.

Figure 12B:
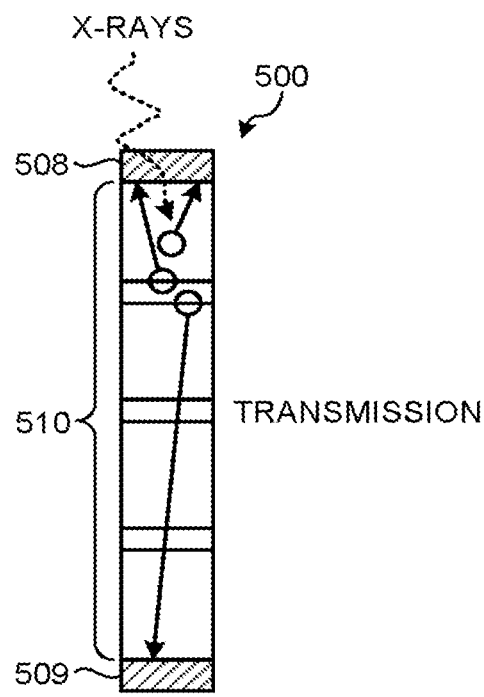
FIG. 12B is a diagram for explaining the detection element according to the fourth embodiment.

FIG. 12B illustrates the case of receiving no instruction to collect scintillator light divided by energy band from the operator. In such a case, all the variable layers 505, 506, and 507 are in the first state of transmitting scintillator light. For this reason, when the scintillators 501, 502, 503, and 504 are referred to as scintillator 510, the scintillator light converted by the scintillator 510 is detected by either of the optical sensor 508 and the optical sensor 509.

Figure 12C:
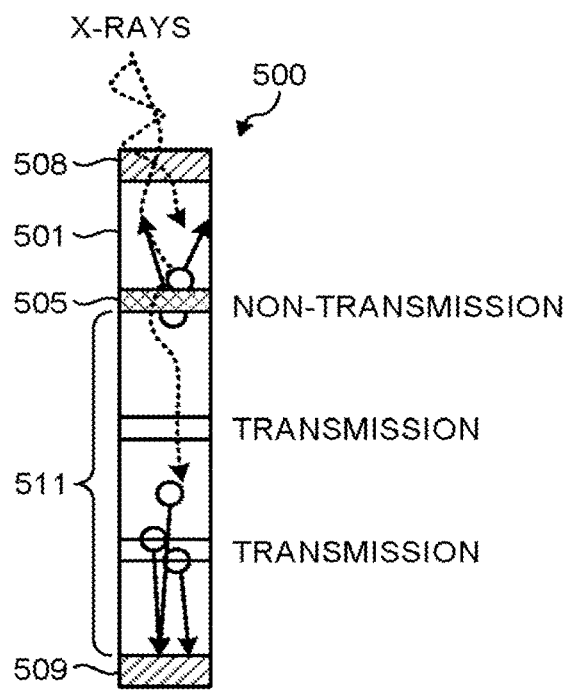
FIG. 12C is a diagram for explaining the detection element according to the fourth embodiment.

FIG. 12C illustrates the case of receiving an instruction to collect scintillator light from the incident X-rays with low energy band and scintillator light from the incident X-rays other than the incident X-rays with low energy band from the operator. In such a case, the switching controller 13b switches the variable layer 505 to the second state. By the switching, the scintillator light converted by the scintillator 501 is detected by the optical sensor 508, because the scintillator light cannot pass through the variable layer 505. In addition, when the scintillators 502, 503, and 504 are referred to as scintillator 511, the scintillator light converted by the scintillator 511 is detected by the optical sensor 509, because the scintillator light cannot pass through the variable layer 505.

Figure 12D:
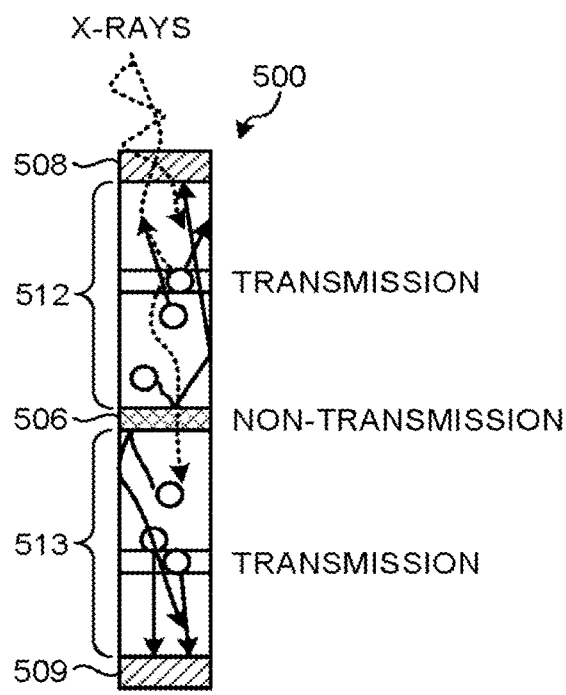
FIG. 12D is a diagram for explaining the detection element according to the fourth embodiment.

FIG. 12D illustrates the case of receiving an instruction from the operator to collect scintillator light in the range from the incident X-rays with low energy band to the incident X-rays with medium energy band, and scintillator light in the range from the incident X-rays with medium energy band to the incident X-rays with high energy band. In such a case, the switching controller 13b switches the variable layer 506 to the second state. By the switching, when the scintillators 501 and 502 are referred to as scintillator 512 and the scintillators 503 and 504 are referred to as scintillator 513, the scintillator light converted by the scintillator 512 is detected by the optical sensor 508, because the scintillator light cannot pass through the variable layer 506. In addition, the scintillator light converted by the scintillator 513 is detected by the optical sensor 509, because the scintillator light cannot pass through the variable layer 506.

Figure 13:
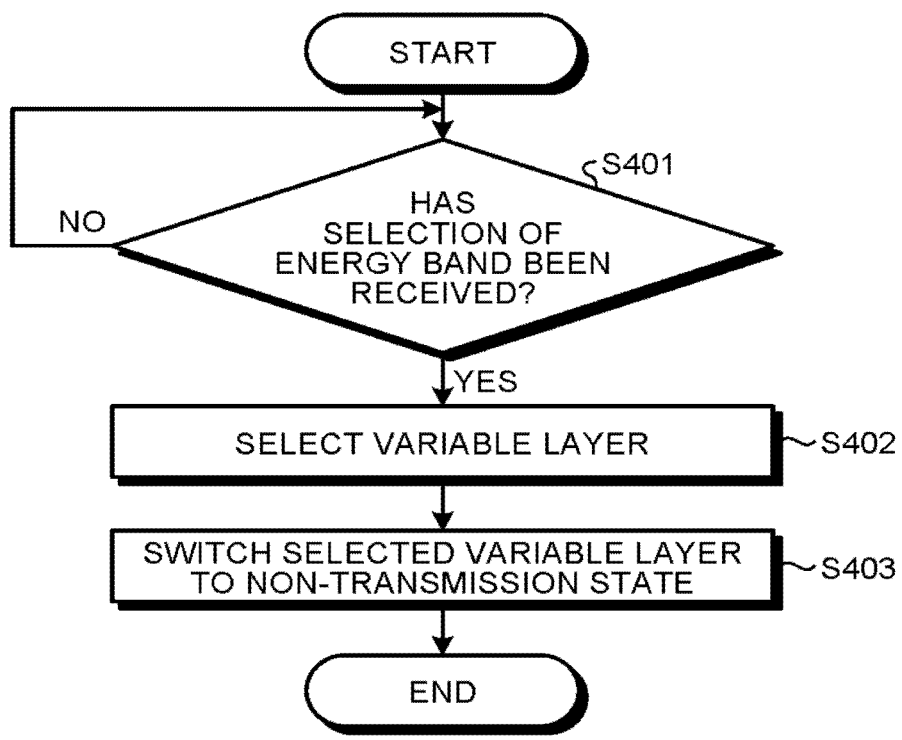
FIG. 13 is a flowchart illustrating a procedure of processing performed by the switching controller according to the fourth embodiment.

FIG. 13 is a flowchart illustrating a procedure of processing performed by the switching controller 13b according to the fourth embodiment. As illustrated in FIG. 13, the switching controller 13b determines whether selection of energy band has been received (Step S401). When the switching controller 13b determines that no selection of energy band has been received (Step S401, No), the switching controller 13b repeatedly determines whether any selection of energy band has been received. By contrast, when the switching controller 13b determines that selection of energy band has been received (Step S401, Yes), the switching controller 13b selects the variable layer (Step S402). The switching controller 13b thereafter switches the selected variable layer to the non-transmission state (Step S403).

The fourth embodiment has the structure of controlling switching of each of the variable layers between the first state and the second state, in accordance with the energy band of the X-rays to be detected. This structure enables collection of scintillator light from the incident X-rays of different energy bands. This structure enables generation of X-ray CT images for discrimination of energies.

In related art, incident X-rays are collected for each of energy bands with a multilayered detector. By contrast, the X-ray CT apparatus according to the fourth embodiment collects incident X-rays for each of energy bands, by switching each of a plurality of variable layers between the transmission state and the non-transmission state. The fourth embodiment with this structure enables simplification of the structure of the detector itself. The fourth embodiment also enables more simplification of the reading circuit at the following stage than a multilayered detector.

Modification of Fourth Embodiment

The fourth embodiment described above illustrates the case of controlling switching of each of the variable layers between the first state and the second state, in accordance with the energy band of the X-rays to be detected. In the meantime, the energy band of the X-rays to be detected is not limited to being identical in all the detection elements. In view of the above, the modification of the fourth embodiment illustrates the case of setting the energy band of the X-rays to be detected to be different between the detection elements that are adjacent in, for example, the row direction.

Figure 14:
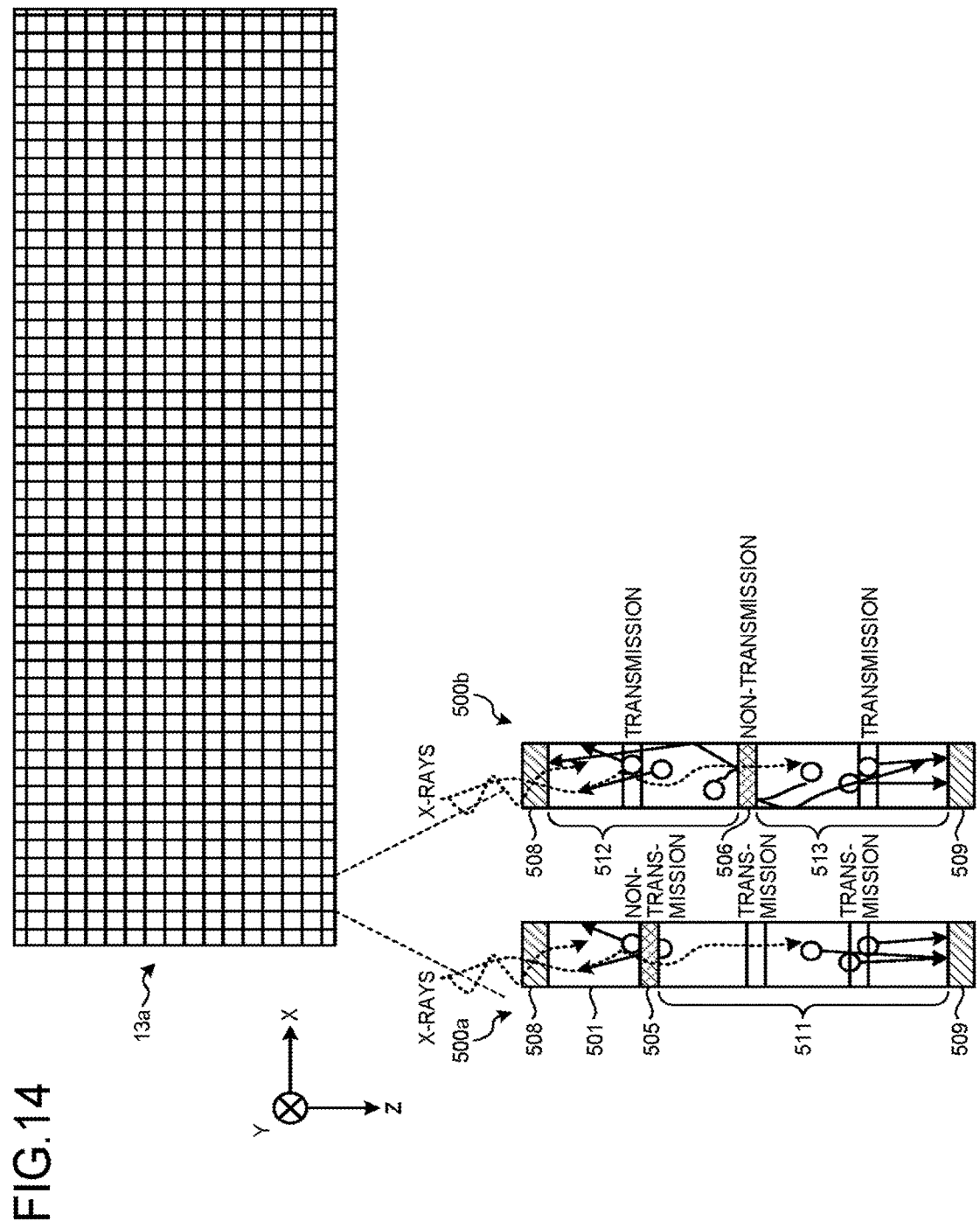
FIG. 14 is a diagram for explaining the switching controller according to a modification of the fourth embodiment.

The X-ray CT apparatus according to the modification of the fourth embodiment has the same configuration as the configuration of the X-ray CT apparatus according to the fourth embodiment, except that part of the function of the switching controller 13b is different. For this reason, the following explanation illustrates only the function of the switching controller 13b according to the modification of the fourth embodiment. FIG. 14 is a diagram for explaining the switching controller 13b according to the modification of the fourth embodiment.

FIG. 14 illustrates the case where the detector 13 is an area detector including a detection element group 13a in which detection elements 500 are arranged in a two-dimensional manner on a surface. In FIG. 14, the detection elements 500 of the detection element group 13a are arranged in a two-dimensional manner in the column direction and the row direction. Supposing that the direction parallel with the X-axis direction is the row direction, the row numbers are successively assigned to the first row, the second row, and the following rows from the upper end of the detection element group 13a along the Z-axis direction. Supposing that the direction parallel with the Z-axis direction is the column direction, the column numbers are successively assigned to the first column, the second column, and the following columns from the left end of the detection element group 13a along the X-axis direction.

Suppose that detection elements 500 located in the column of an odd number are referred to as detection elements 500a, and detection elements 500 located in the column of an even number are referred to as detection elements 500b. Specifically, even when the detection elements 500 are located in any row, detection elements 500 located in the column of an odd number are referred to as detection elements 500a, and detection elements 500 located in the column of an even number are referred to as detection elements 500b. The structure of the detection elements 500a and 500b is the same as the structure of the detection element 500 illustrated in FIG. 12A.

The switching controller 13b according to the modification of the fourth embodiment performs control to cause the energy band of the X-rays to be detected to be different between the detection elements that are adjacent in the row direction. For example, when the system controller 38 receives an instruction from the operator via the input device 31 to collect scintillator light such that energy bands of the X-rays to be detected are different between the detection elements that are adjacent in the row direction, the system controller 38 instructs the switching controller 13b of the detector 13 via the scan controller 33 to switch each of the variable layers of the detection elements 500a and the detection elements 500b between the first state and the second state such that the energy bands to be collected are different between the detection elements 500a and the detection elements 500b.

More specifically, as illustrated in FIG. 14, the switching controller 13b controls each detection element 500a in the same manner as the detection element 500 as illustrated in FIG. 12C, and controls each detection element 500b in the same manner as the detection element 500 as illustrated in FIG. 12D. FIG. 14 illustrates the case based on the supposition that each detection element 500a and each detection element 500b do not use the optical sensor 508, but use only the optical sensor 509. Specifically, the detection elements are prevented from collecting scintillator light of the incident X-rays of the energy band that easily causes pileup. With this structure, for example, each detection element 500a collects scintillator light of incident X-rays other than the incident X-rays with low energy band, among the incident X-rays with low energy band and incident X-rays other than the incident X-rays with low energy band. Each detection element 500b collects scintillator light of incident X-rays in the range from the incident X-rays with medium energy band to the incident X-rays with high energy band, among incident X-rays in the range from the incident X-rays with low energy band to the incident X-rays with medium energy band, and incident X-rays in the range from the incident X-rays with medium energy band to the incident X-rays with high energy band.

As described above, the energy bands of X-rays to be detected are set different between the detection elements that are adjacent in the row direction. This structure enables control such that the detector 13 has two different detection elements.

The above embodiment illustrates the case of setting energy bands of X-rays to be detected to be different between the detection elements that are adjacent in the row direction, but the embodiments are not limited to this. For example, the switching controller 13b may control switching of each of the variable layers in each detection element between the first state and the second state such that energy bands of X-rays to be detected are different between detection elements that, are adjacent in a certain direction. More specifically, the switching controller 13b may perform control such that energy bands of X-rays to be detected are different between detection elements that are adjacent in the column direction. Otherwise, the switching controller 13b may perform control such that energy bands of X-rays to be detected are different between detection elements that are adjacent in the column direction and the row direction.

Fifth Embodiment

The first to the fourth embodiments described above illustrate that the switching controller 13b switches the variable layer between the first state and the second state. For example, when each variable layer is formed of liquid crystal, the switching controller 13b switches the variable layer between the first state and the second state, by controlling the voltage applied to the liquid crystal. A fifth embodiment, illustrates a power supply path to a variable layer that is controlled when the switching controller 13b switches the variable layer between the first state and the second state.

Figure 15:
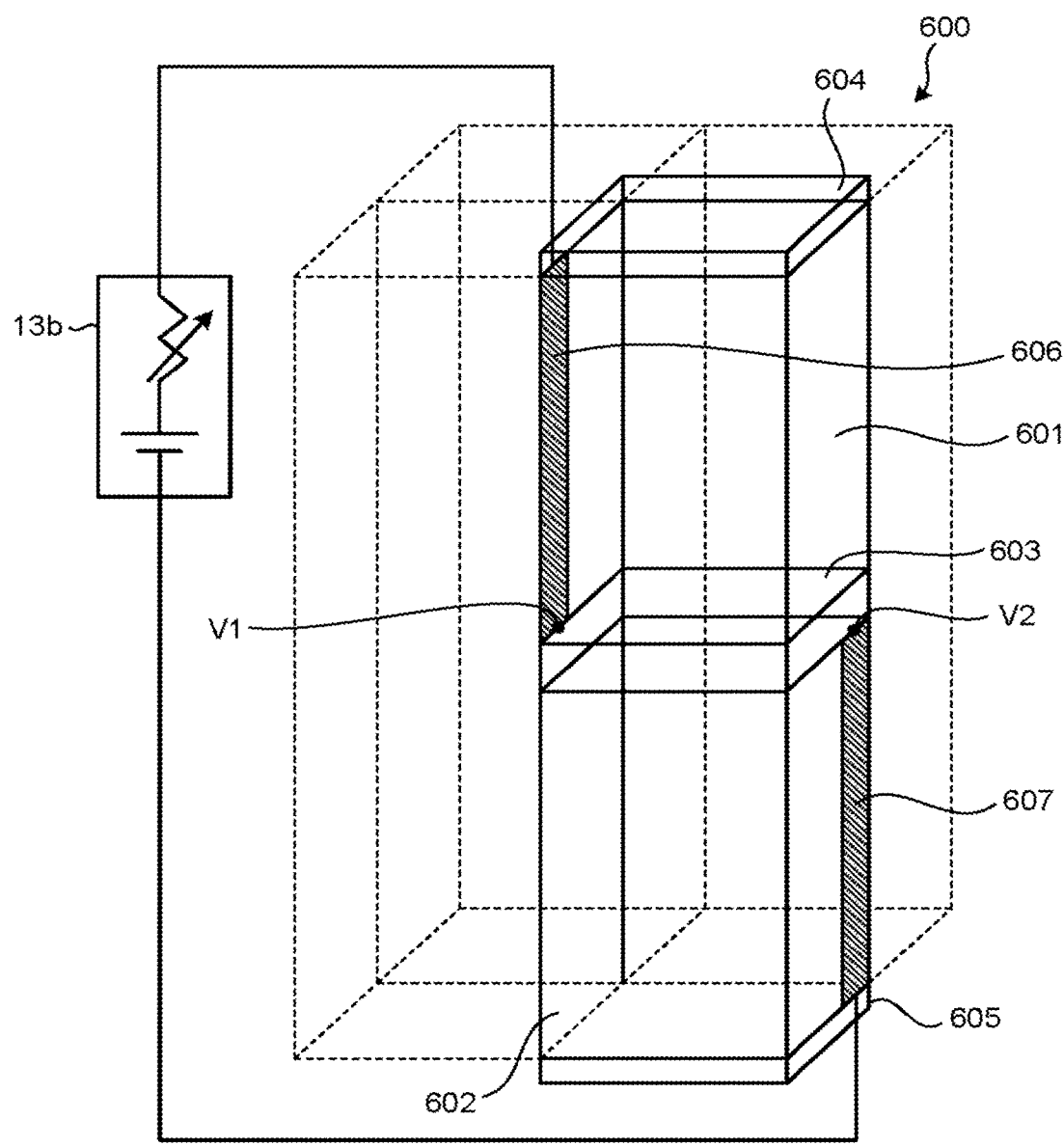
FIG. 15 is a diagram for explaining a detection element according to a fifth embodiment.

FIG. 15 is a diagram for explaining each detection element according to the fifth embodiment. FIG. 15 illustrates the case where the switching controller 13b switches each of the variable layers in the detection element group formed of a plurality of detection elements between the first state and the second state for each detection element group together. Although FIG. 15 illustrates only four detection elements as the detection element group, the number of detection elements included in the detection element group can be changed to a desired number. For the sake of convenience of explanation, only one detection element 600 among the four detection elements is illustrated with solid lines, and the other three detection elements are illustrated with broken lines.

As illustrated in FIG. 15, each detection element 600 according to the fifth embodiment includes scintillators 601 and 602, optical sensors 604 and 605, and a variable layer 603. A thin layer serving as a separator is applied to the detection element 600 to prevent, transmission of light to the scintillator of the adjacent detection element. The separator is a stable chemical substance with high reflectivity, and applied to the whole surface of the detection element 600. In the fifth embodiment, wires 606 and 607 to the power supply are buried in the separator. For example, the wire 606 connects the anode with an upper region V1 of the variable lever 603. The wire 607 is buried in a surface opposed to the surface in which the wire 606 is buried, and connects the cathode with a lower region V2 of the variable layer 603. The variable layer 603 is in the first state of transmitting scintillator light, when no potential difference exists between the upper surface thereof including the region V1 and the lower surface thereof including the region V2. The switching controller 13b turns on the power supply included in the switching controller 13b, to generate a potential difference between the upper surface and the lower surface of the variable layer 603, and switches the variable layer 603 from the first state to the second state. In the example illustrated in FIG. 15, the switching controller 13b is provided for each detection element group.

Modification of Fifth Embodiment

Figure 16:
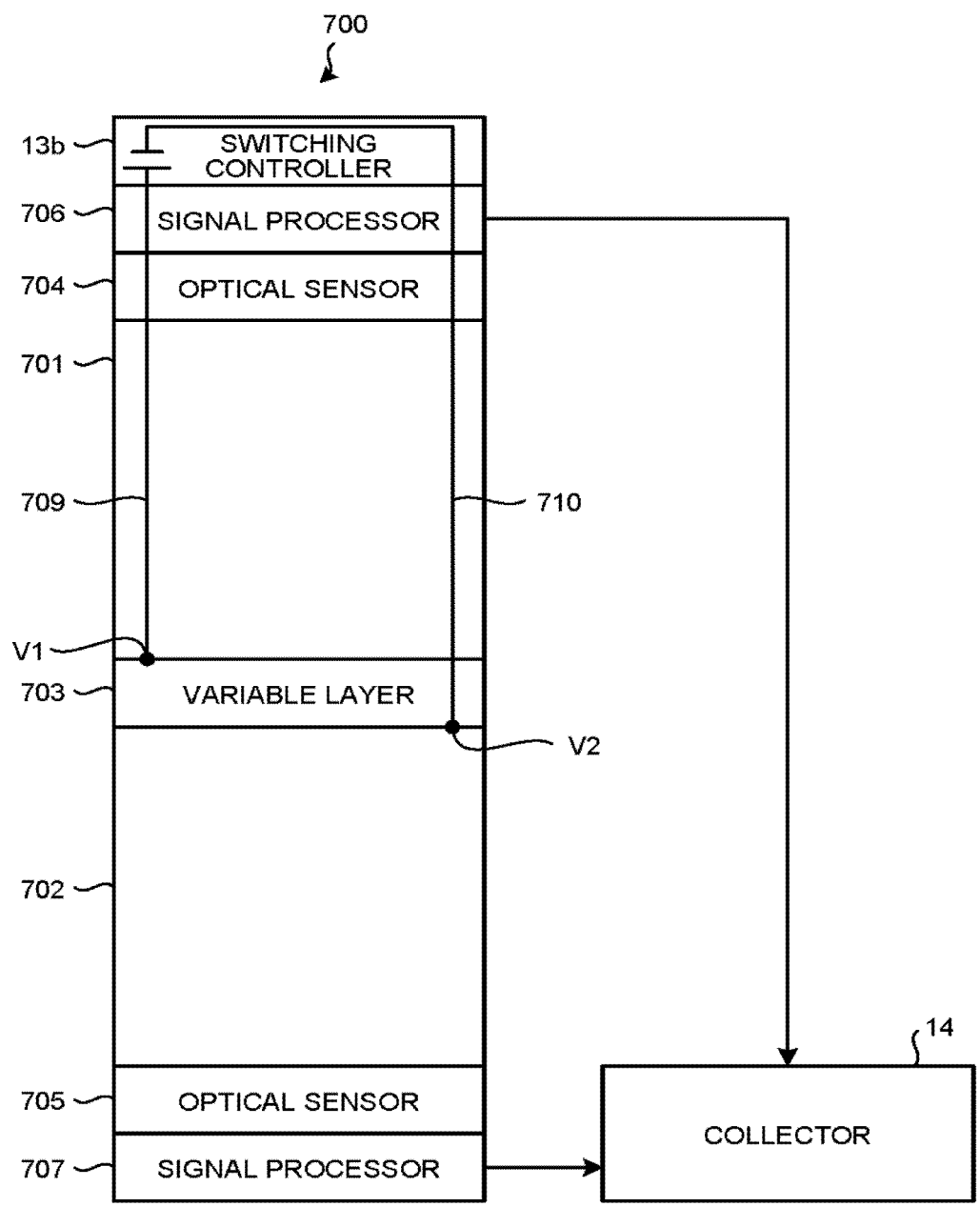
FIG. 16 is a diagram for explaining another example of a detection element according to a modification of the fifth embodiment.

The switching controller 13b may switch the variable layer between the first state and the second state for each of the individual elements. FIG. 16 is a diagram for explaining each detection element according to the modification of the fifth embodiment. As illustrated in FIG. 16, each detection element 700 according to the modification of the fifth embodiment includes scintillators 701 and 702, optical sensors 704 and 705, and a variable layer 703.

Each of the optical sensors 704 and 705 included in each detection element 700 is provided with a substrate. The substrate of the optical sensor 704 includes a signal processor 706 that receives input of an analog signal serving as a counting result obtained by the optical sensor 704, converts the received analog signal into a digital signal, and outputs the digital signal as an output signal to the collector 14. In the same manner, the substrate of the optical sensor 705 includes a signal processor 707 that receives input of an analog signal serving as a counting result obtained by the optical sensor 705, converts the received analog signal into a digital signal, and outputs the digital signal as an output signal to the collector 14. Also in the first to the fourth embodiments described above, each optical sensor included in each detection element is provided with a substrate including a signal processor that outputs the light counted by the optical sensor as an output signal to the collector 14, in the same manner.

The substrate included in each detection element 700 according to the modification of the fifth embodiment is also provided with the switching controller 13*b*. In other words, the switching controller 13*b* according to the modification of the fifth embodiment is provided in each of the detection elements. The switching controller 13*b* switches the variable layer 703 between the first state and the second state, by performing control to turn on and off the power supply. More specifically, a separator is applied to each detection element 700, in the same manner as the detection element 600 illustrated in FIG. 15. Wires 709 and 710 are buried in the separator. For example, the wire 709 connects the anode in the switching controller 13*b* with an upper region V1 of the variable layer 703. The wire 710 is buried in a surface opposed to the surface in which the wire 709 is buried, and connects the cathode in the switching controller 13*b* with a lower region V2 of the variable layer 703. The variable layer 703 is in the first state of transmitting scintillator light, when no potential difference exists between the upper surface thereof including the region V1 and the lower surface thereof including the region V2. The switching controller 13*b* turns on the power supply, to generate a potential difference between the upper surface and the lower surface of the variable layer 703, and switches the variable layer 703 from the first state to the second state. When each detection element is provided with a plurality of variable layers, each of the variable layers is provided with wires connected to the anode and the cathode. The switching controller 13*b* is provided with a switch to switch a combination of wires to be connected to the anode and the cathode, and thereby controls switching of each of the variable layers between the first state and the second state. The switching controller 13*b* according to the modification of the fifth embodiment is provided on, for example, the substrate provided with a signal processor 807, and can be controlled by a control signal from the scan controller 33.

Other Embodiments

Embodiments are not limited to the embodiments described above.

Figure 17:
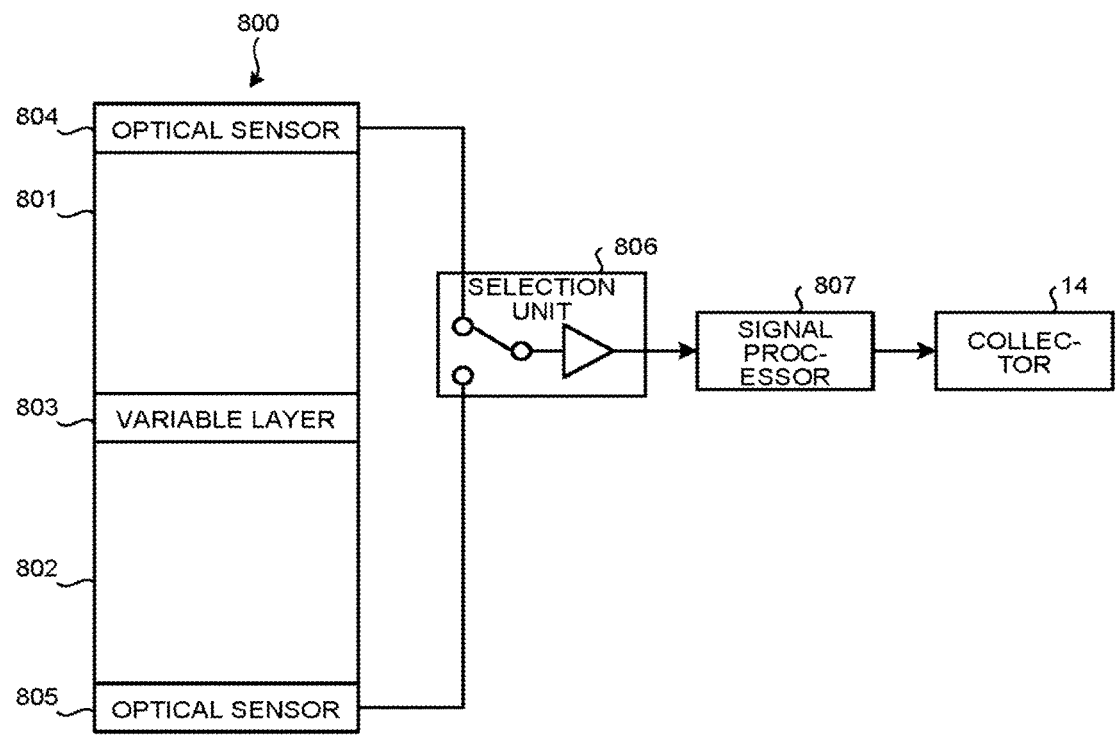
FIG. 17 is a diagram for explaining a detection element according to another embodiment.

Although the embodiments described above illustrate the structure in which each of the optical sensors is provided with a signal processor, the embodiments are not limited to these. For example, each detection element may include only one signal processor for two optical sensors. FIG. 17 is a diagram for explaining each detection element 800 according to another embodiment. FIG. 17 illustrates the case of selecting and using one of measurement results of the two optical sensors. As illustrated in FIG. 17, each detection element 800 includes scintillators 801 and 802, a variable layer 803, and optical sensors 804 and 805. Each of the optical sensors 804 and 805 outputs a counting result as an analog signal to a selection unit 806. The selection unit 806 receives input of analog signals from the optical sensors 804 and 805, and outputs one of the received analog signals to the signal processor 807. The selection unit 806 is provided on, for example, the substrate provided with the signal processor 807, and can be controlled by a control signal from the scan controller 33.

The selection unit 806 determines which of the analog signals from the optical sensors 804 and 805 should be received, based on, for example, imaging conditions. More specifically, the selection unit 806 determines which of the analog signal should be received, according to the imaged region. For example, specifically, in the case of performing imaging specialized for soft tissues such as the breast and the digestive system, the selection unit 806 receives input of an analog signal from the optical sensor 804, and outputs the received analog signal to the signal processor 807. For example, in the case of performing imaging with counts of incident X-rays having high energy band, such as bones, the selection unit 806 receives input of an analog signal from the optical sensor 805, and outputs the received analog signal to the signal processor 807. The selection unit 806 may receive, from the operator, an instruction that designates which of the analog signals from the optical sensors 804 and 805 should be received. The signal processor 807 thereafter converts the analog signal received from the selection unit 806 into a digital signal, and outputs the digital signal as an output signal to the collector 14. The image reconstructing unit 36 generates an X-ray CT image based on at least one of the signals that are output from the respective optical sensors disposed at both ends of the scintillator in the X-ray incident direction thereof. With this structure, the X-ray CT apparatus can reconstruct an X-ray CT image suitable for the imaging conditions. In addition, because each detection element has only one signal processor for the two optical sensors, the number of signal lines between the signal processor 807 and the collector 14 can be reduced.

When each detection element, is configured to have only one signal processor for the two optical sensors, each detection element may be configured to use both the counting results that are output from the two optical sensors. In such a case, the selection unit 806 outputs the analog signals received from the two optical sensors to the collector 14 together. Because the counting results that are output from the two optical sensors are output to the collector 14 together, the output signal can be supplemented when, for example, the dose of the incident X-rays is low.

Figure 18:
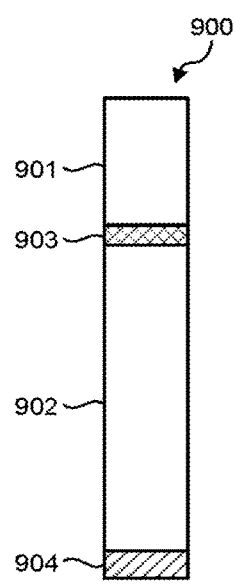
FIG. 18 is a diagram for explaining a detection element according to another embodiment.

Although the embodiments described above illustrate that each detection element includes optical sensors at both ends thereof, the embodiments are not limited to these. For example, each detection element may include an optical sensor in only one end portion. FIG. 18 is a diagram for explaining a detection element 900 according to another embodiment. For example, as illustrated in FIG. 18, each detection element 900 includes scintillators 901 and 902, a variable layer 903, and an optical sensor 904. Specifically, each detection element 900 includes the optical sensor 904 in an end portion distant from the X-ray tube 12 serving as the X-ray source, and has no optical sensor in an end portion close to the X-ray tube 12 serving as the X-ray source. In other words, the optical sensor 904 is disposed in one end portion out of the end portions in the X-ray incident direction of the scintillator. In such a case, the optical sensor 904 outputs the counting result as analog signal to the signal processor. The signal processor converts the analog signal received from the optical sensor 904 into a digital signal, and outputs the digital signal as an output signal to the collector 14. In such a case, the switching controller 13*b* controls switching of the variable layer, when the determination item is equal to or higher than a predetermined threshold. Examples of the determination item include the set value that is set as imaging conditions, the intensity of the signal detected by the X-ray detector, the upper limit of the energy band of the emitted X-rays determined based on the imaging conditions, and the number of counts of signals having an energy band equal to or higher than a predetermined energy value among the signals detected by the X-ray detector. Each detection element 900 configured as described above may switch the variable layer 903 to the second state in which the variable layer 903 does not transmit scintillator light, without determining, for example, whether the determination item is equal to or higher than the predetermined threshold. With this structure, the optical sensor 904 can count only the incident X-rays having an energy band equal to or higher than the predetermined threshold, without counting the incident X-rays having an energy band lower than the predetermined threshold. As a result, the image reconstructing unit 36 can reconstruct X-ray CT image data with reduced noise, and an X-ray CT image visualizing bones by counting the incident X-rays having high energy band. Although the example in FIG. 18 illustrates the case where the detection element 900 includes the optical sensor 904 only in the end portion distant from the X-ray tube 12, the embodiments are not limited to this. For example, the detection element 900 may include the optical sensor 904 only in the end portion close to the X-ray tube 12. In addition, the detection element 900 configured as described above can count only incident X-rays specialized for the soft tissue by, for example, performing imaging with the variable layer 903 switched to the second state in which the variable layer 903 does not transmit scintillator light. Specifically, the detection element 900 does not count incident X-rays with high energy band such as X-rays transmitted through bones. With this structure, the image reconstructing unit 36 can reconstruct, for example, X-ray CT image data visualizing only the breast or the digestive system.

In the above embodiments, the switching controller 13b has been explained with the structure of controlling switching of the variable layer when the determination item is equal to or higher than the predetermined threshold. The itching controller 13b controls switching of the variable layer in each view, when the threshold determination processing is performed in real time. Specifically, when the switching controller 13b determines that the determination item exceeds the threshold value as a result of threshold determination processing in a view, the switching controller 13b switches the variable layer to the second state in the next view.

The switching controller 13b may set in advance the time of switching the variable layer to the second state. For example, the switching controller 13b specifies the imaging section in which the intensity of the signal detected by the X-ray detector is equal to or higher than the predetermined threshold based on the scanogram, and switches the variable layer to the second state in the imaging section.

Although the above embodiments illustrate that the switching controller 13b switches one of the variable layers to the second state in which the variable layer does not transmit scintillator light, the embodiments are not limited to these. For example, the switching controller 13b may perform control to cause a plurality of variable layers to be simultaneously switched to the second state.

Although the first to the fourth embodiments described above illustrate that the optical sensors in each detection element are arranged at both ends in the X-ray incident direction of the scintillator, the embodiments are not limited to these. For example, no optical sensor may be disposed in the end portion on the X-ray incident side of the scintillator in the detection element.

Although the first to the fourth embodiments described above have been explained on the supposition that each variable layer is in the first state of transmitting scintillator light, at the start of imaging performed by the X-ray CT apparatus, the embodiments are not limited to these. For example, any of the variable layers may be in the second state in which the variable layer does not transmit scintillator light, at the start of imaging performed by the X-ray CT apparatus. In addition, a plurality of variable layers may be controlled to be simultaneously switched to the second state at the start of imaging performed by the X-ray CT apparatus.

Although the embodiments described above illustrate that the detector is included in an X-ray CT apparatus, the embodiments are not limited to these. For example, the detector may be included in an X-ray diagnostic apparatus. In such a case, the X-ray diagnostic apparatus includes the detector and an image generator. The detector includes a scintillator converting incident X-rays radiated from an X-ray source into scintillator light, an optical sensor detecting the converted scintillator light, a variable layer that is provided in the scintillator and switchable between a first state of transmitting scintillator light and a second state of transmitting no scintillator light, and a switching controller controlling switching of the variable layer between the first state and the second state. The image generator generate an X-ray image based on a signal output from the detector.

All or an arbitrary part of the processing functions performed by each apparatus can be provided by a central processing unit (CPU) and a computer program analyzed and excused by the CPU or provided as hardware by wired logic.

At least one of the embodiments explained above enables reduction in occurrence of counting loss of incident X-rays.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computer tomography (CT) apparatus, comprising:
    an X-ray source configured to radiate X-rays;
    an X-ray detector including a scintillator including a first region close to the X-ray source and a second region distant from the X-ray source, at least one optical sensor configured to detect scintillator light obtained by converting the X-rays radiated from the X-ray source with the scintillator, and a variable layer that is provided in the scintillator and switchable between a first state in which the variable layer transmits the scintillator light between the first region and the second region and a second state in which the variable layer does not transmit the scintillator light between the first region and the second region;
    switching control circuitry configured to switch the variable layer between the first state and the second state during application of the X-rays; and
    generating circuitry configured to generate a CT image based on a signal output from the X-ray detector.

2. The X-ray CT apparatus according to claim 1, wherein the at least one optical sensor includes two optical sensors, disposed at opposite ends of the scintillator in an X-ray incident direction.

3. The X-ray CT apparatus according to claim 1, wherein the at least one optical sensor includes one optical sensor disposed at one end of the scintillator in an X-ray incident direction.

4. The X-ray CT apparatus according to claim 1, wherein the switching control circuitry is further configured to switch the variable layer to the second state when a set value that is set as an imaging condition is equal to or higher than a predetermined threshold.

5. The X-ray CT apparatus according to claim 1, wherein the switching control circuitry is further configured to switch the variable layer to the second state when an intensity of a signal detected by the X-ray detector is equal to or higher than a predetermined threshold.

6. The X-ray CT apparatus according to claim 1, wherein the switching control circuitry is further configured to switch the variable layer to the second state when an upper limit of an energy band of emitted X-rays determined based on an imaging condition is equal to or higher than a predetermined threshold.

7. The X-ray CT apparatus according to claim 1, wherein the switching control circuitry is further configured to switch the variable layer to the second state when a number of counts of signals having an energy band equal to or higher than a predetermined energy value among signals detected by the X-ray detector is equal to or higher than a predetermined threshold.

8. The X-ray CT apparatus according to claim 1, further comprising an additional variable layer, which is disposed in at least one of the first region and the second region in the scintillator.

9. The X-ray CT apparatus according to claim 8, wherein the switching control circuitry is further configured to control switching of each of the variable layers between the first state and the second state, in accordance with an intensity of a signal detected by the X-ray detector.

10. The X-ray CT apparatus according to claim 9, wherein, when the intensity of the signal detected by the X-ray detector exceeds any of a plurality of thresholds set for the intensity of the signal, the switching control circuitry refers to association information that associates the thresholds with the respective variable layers, specifies a specific variable layer, of the variable layers, associated with a threshold of a highest value among the thresholds that the intensity of the signal exceeds, and switches the specified variable layer to the second state.

11. The X-ray CT apparatus according to claim 8, wherein the switching control circuitry is further configured to refer to, when a set value that is set as an imaging condition exceeds any of a plurality of thresholds that are set for the imaging condition, association information that associates the thresholds with the respective variable layers, specify a specific variable layer, of the variable layers, associated with a threshold of a highest value among the thresholds that the set value exceeds, and switch the specified variable layer to the second state.

12. The X-ray CT apparatus according to claim 8, wherein the switching control circuitry is further configured to classify intensities of the incident X-rays based on a scanogram, specify a specific variable layer, of the variable layers, with reference to association information that associates the classified intensities of the incident X-rays with the respective variable layers, and switch the specified variable layer to the second state.

13. The X-ray CT apparatus according to claim 8, wherein the switching control circuitry is further configured to refer to, when an upper limit of an energy band of emitted X-rays determined based on an imaging condition exceeds any of a plurality of thresholds that are set for the upper limit, association information that associates the thresholds with the respective variable layers, specify a specific variable layer, of the variable layers, associated with a threshold of a highest value among the thresholds that the upper limit exceeds, and switch the specified variable layer to the second state.

14. The X-ray CT apparatus according to claim 8, wherein the switching control circuitry is further configured to refer to, when a number of counts of signals having an energy band equal to or higher than a predetermined energy value among signals detected by the X-ray detector exceeds any of a plurality of thresholds that are set for the number of counts of signals, association information that associates the thresholds with the respective variable layers, specify a variable layer, of the variable layers, associated with a threshold of a highest value among the thresholds that the number of counts of signals exceeds, and switch the specified variable layer to the second state.

15. The X-ray CT apparatus according to claim 8, further comprising receiving circuitry configured to receive setting of an energy band of X-rays to be collected,
wherein the switching control circuitry is further configured to control switching of each of the variable layers between the first state and the second state, in accordance with the energy band, the setting of which has been received by the receiving circuitry.

16. The X-ray CT apparatus according to claim 15, wherein the switching control circuitry controls switching of each of the variable layers in each detection element between the first state and the second state, to enable detection of incident X-rays of energy bands that are different between detection elements that are adjacent in a predetermined direction.

17. The X-ray CT apparatus according to claim 1, wherein the at least one optical sensor includes two optical sensors disposed at opposite ends of the scintillator, and the generating circuitry generates the CT image based on at least one of signals that are output from the two optical sensors.

18. The X-ray CT apparatus according to claim 1, wherein a plurality of detection elements, each of which includes the scintillator, the optical sensor, and the variable layer, are arranged in a two-dimensional manner on a surface.

19. An X-ray computer tomography (CT) apparatus comprising:
an X-ray source configured to radiate X-rays;
an X-ray detector including a scintillator including a first region close to the X-ray source and a second region distant from the X-ray source, an optical sensor configured to detect scintillator light obtained by converting the X-rays radiated from the X-ray source with the scintillator, and a variable layer that is provided in the scintillator and switchable between a first state in which the variable layer transmits the scintillator light between the first region and the second region and a second state in which the variable layer does not transmit the scintillator light between the first region and the second region;
generating circuitry configured to generate a CT image based on a signal output from the X-ray detector; and
switching control circuitry configured to specify an imaging time period in which an intensity of a signal detected by the X-ray detector is equal to or higher than a predetermined threshold based on a scanogram, and switch the variable layer to the second state in the imaging time period.

20. An X-ray computer tomography (CT) apparatus, comprising:
- an X-ray source configured to radiate X-rays;
- an X-ray detector including a scintillator, an optical sensor configured to detect scintillator light obtained by converting the X-rays radiated from the X-ray source with the scintillator, and variable layers that are provided in the scintillator, each of the variable layers separating the scintillator into a first region close to the X-ray source and a second region distant from the X-ray and being switchable between a first state in which the scintillator light transmits between the first region and the second region and a second state in which the scintillator light does not transmit between the first region and the second region;
- receiving circuitry configured to receive setting of an energy band of X-rays to be collected;
- switching control circuitry configured to control switching of each of the variable layers between the first state and the second state, in accordance with the energy band, the setting of which has been received by the receiving circuitry; and
- generating circuitry configured to generate a CT image based on a signal output from the X-ray detector, wherein
- the switching control circuitry controls switching of each of the variable layers in each detection element between the first state and the second state, to enable detection of incident X-rays of energy bands that are different between detection elements that are adjacent in a predetermined direction.

21. An X-ray computer tomography (CT) apparatus, comprising:
- an X-ray source configured to radiate X-rays;
- an X-ray detector including a scintillator, an optical sensor configured to detect scintillator light obtained by converting the X-rays radiated from the X-ray source with the scintillator, and variable layers that are provided in the scintillator, each of the variable layers separating the scintillator into a first region close to the X-ray source and a second region distant from the X-ray and being switchable between a first state in which the scintillator light transmits between the first region and the second region and a second state in which the scintillator light does not transmit between the first region and the second region;
- switching control circuitry configured to set thresholds regarding intensity of incident X-rays and switch each of the variable layers between the first state and the second state by referring to association information that associates each of the thresholds with each of the variable layers; and
- generating circuitry configured to generate a CT image based on a signal output from the X-ray detector.

* * * * *